US011826493B2

(12) United States Patent
Grossman et al.

(10) Patent No.: US 11,826,493 B2
(45) Date of Patent: Nov. 28, 2023

(54) ANTIMICROBIAL COATINGS FOR MEDICAL IMPLEMENTS AND MEDICAL DEVICES

(71) Applicant: Allied Bioscience, Inc., Plano, TX (US)

(72) Inventors: Craig Grossman, Point Roberts, WA (US); Gavri Grossman, Dallas, TX (US); Daniel Moros, New York, NY (US); Misagh Alipour, Surrey (CA); Jie Fang, Ammon, ID (US)

(73) Assignee: SRFC BIO, INC., Plano, TX (US)

( * ) Notice: Subject to any disclaimer, the term of this patent is extended or adjusted under 35 U.S.C. 154(b) by 74 days.

(21) Appl. No.: 17/351,453

(22) Filed: Jun. 18, 2021

(65) Prior Publication Data

US 2021/0308339 A1    Oct. 7, 2021

Related U.S. Application Data

(63) Continuation of application No. 15/938,417, filed on Mar. 28, 2018, now Pat. No. 11,077,234.

(60) Provisional application No. 62/477,885, filed on Mar. 28, 2017.

(51) Int. Cl.
| | |
|---|---|
| *A61L 29/16* | (2006.01) |
| *A01N 55/00* | (2006.01) |
| *A61L 29/02* | (2006.01) |
| *A61L 29/08* | (2006.01) |
| *A61L 29/06* | (2006.01) |
| *A61L 31/08* | (2006.01) |
| *A61L 31/16* | (2006.01) |

(52) U.S. Cl.
CPC .............. *A61L 29/16* (2013.01); *A01N 55/00* (2013.01); *A61L 29/02* (2013.01); *A61L 29/06* (2013.01); *A61L 29/08* (2013.01); *A61L 31/08* (2013.01); *A61L 31/16* (2013.01); *A61L 2300/202* (2013.01); *A61L 2300/404* (2013.01); *A61L 2300/606* (2013.01); *A61L 2300/802* (2013.01); *A61L 2420/02* (2013.01); *A61L 2420/06* (2013.01)

(58) Field of Classification Search
CPC .......... A61L 29/16; A61L 31/16; A61L 29/08; A61L 31/08; A61L 2420/02; A61L 2420/06
See application file for complete search history.

(56) References Cited

U.S. PATENT DOCUMENTS

| | | | | |
|---|---|---|---|---|
| 4,917,686 A | * | 4/1990 | Bayston | A61L 27/54 604/265 |
| 6,143,037 A | * | 11/2000 | Goldstein | A61L 31/10 977/890 |
| 6,364,909 B1 | * | 4/2002 | McGee | A61F 2/32 623/16.11 |
| 9,528,009 B2 | | 12/2016 | Grossman et al. | |
| 9,550,689 B2 | | 1/2017 | Grossman | |
| 9,757,769 B2 | | 9/2017 | Grossman et al. | |
| 9,849,207 B2 | | 12/2017 | Grossman | |
| 9,855,584 B2 | | 1/2018 | Grossman et al. | |
| 9,856,360 B2 | | 1/2018 | Moros et al. | |
| 9,918,475 B2 | | 3/2018 | Moros et al. | |
| 2007/0048345 A1 | | 3/2007 | Huang et al. | |
| 2007/0154621 A1 | * | 7/2007 | Raad | A61L 29/16 427/2.1 |
| 2010/0179475 A1 | * | 7/2010 | Hoffmann | A61L 29/16 427/2.3 |
| 2013/0312757 A1 | | 11/2013 | Cragg et al. | |
| 2016/0317771 A1 | | 11/2016 | Klee et al. | |
| 2018/0055880 A1 | | 3/2018 | Adamy et al. | |

FOREIGN PATENT DOCUMENTS

| | | | |
|---|---|---|---|
| GB | 2309387 | 8/1999 | |
| WO | 2016073634 | 5/2016 | |
| WO | WO-2016073634 A1 * | 5/2016 | ............... B05D 1/02 |

OTHER PUBLICATIONS

ISA; International Search Report and Written Opinion dated Jun. 1, 2018 in International Application No. PCT/US18/24657.
ISA; International Preliminary Report on Patentability dated Feb. 22, 2019 in International Application No. PCT/US2018/024657.
USPTO; Restriction Requirement dated Feb. 19, 2019 in U.S. Appl. No. 15/938,417.
USPTO; Non-Final Office Action dated Jun. 26, 2019 in U.S. Appl. No. 15/938,417.
USPTO; Final Office Action dated Dec. 26, 2019 in U.S. Appl. No. 15/938,417.
USPTO; Advisory Action dated Apr. 6, 2020 in U.S. Appl. No. 15/938,417.
USPTO; Non-Final Office Action dated Jun. 11, 2020 in U.S. Appl. No. 15/938,417.
USPTO; Final Office Action dated Nov. 10, 2020 in U.S. Appl. No. 15/938,417.
USPTO; Advisory Action dated Dec. 16, 2020 in U.S. Appl. No. 15/938,417.
USPTO; Non-Final Office Action dated Apr. 29, 2021 in U.S. Appl. No. 15/938,417.
USPTO; Notice of Allowance dated May 14, 2021 in U.S. Appl. No. 15/938,417.

* cited by examiner

*Primary Examiner* — Michael B. Pallay
(74) *Attorney, Agent, or Firm* — Snell & Wilmer L.L.P.

(57) ABSTRACT

The present disclosure provides antimicrobial coating compositions that are used to form residual antimicrobial coatings on medical implements and medical devices including the components of medical equipment such as CPAP/BiPAP machines. Antimicrobial coating compositions comprise at least one of an organosilane $(R^1O)_3Si—R^2—Z$, an organic amine $R^9R^{10}R^{11}N$, a titanium (IV) species, a 1,2-diol, an α-hydroxy acid, a β-hydroxy acid, and an organosilane grafted parylene polymer, wherein $R^1$ is H, alkyl, substituted alkyl, aryl or substituted aryl, $R^2$ is a bivalent linker, Z is a nucleophile, leaving group, or quaternary nitrogen substituent, and $R^9$, $R^{10}$, and $R^{11}$ are independently H, alkyl, substituted alkyl, aryl, substituted aryl or cyclic.

18 Claims, No Drawings

ANTIMICROBIAL COATINGS FOR MEDICAL IMPLEMENTS AND MEDICAL DEVICES

CROSS-REFERENCE TO RELATED APPLICATIONS

This application is a continuation of U.S. Non-Provisional application Ser. No. 15/938,417 filed Mar. 28, 2018 and entitled "Antimicrobial Coatings for Medical Implements and Medical Devices," (now U.S. Pat. No. 11,077,234). The '417 application claims priority to, and the benefit of U.S. Provisional Patent Application Ser. No. 62/477,885 filed Mar. 28, 2017 and entitled "Non-leaching Antimicrobial Coatings for Medical Implements and Medical Devices." These disclosures are incorporated herein by reference in their entireties for all purposes.

FIELD

The present disclosure relates to medical implements such as surgical tools and medical devices including implantable devices and portable equipment. In particular, the present disclosure relates to antimicrobial coatings for medical implements and medical devices including parts to medical equipment.

BACKGROUND

Infection resistant coatings have the potential to minimize risk of hospital acquired infections. For implanted medical devices, antimicrobial coatings may reduce device-associated infections and may provide short or long term benefits to patients receiving an implantable medical device. For example, an antimicrobial coating may provide a temporary safeguard for the days after surgery, or in some cases, may exhibit a lifetime of resistance to microbial buildup. Additionally, medical implements, such as surgical tools, may benefit from having infection resistant coatings even though the implements are autoclaved prior to use. The risk exists that even an initially autoclaved implement will pick up a pathogen just prior to or during a medical procedure, enabling the possibility for pathogen transmission to the patient undergoing the procedure or to other patients. Further, medical equipment, even in a residential environment such as CPAP machines, may harbor pathogens, especially since components of home devices are not subject to hospital level sterilization procedures.

Several antimicrobial coatings for medical devices are known. For example, Bacticent® CHX, available from Harland Medical Systems, Eden Prairie, MN, is a heat-cured co-polymer matrix infused with chlorhexidine diacetate. Other coatings are based on silver sulfadiazine. For example, Coatings2Go, (or "C2G"), Carlisle, MA, provides a coating comprising silver sulfadiazine in a hydrophilic polymer mixture of 1,6-diisocyanatohexane homopolymer, N-methyl-2-pyrrolidone; polyisocyanate, and hexamethylene-di-isocyanate. Another coating is provided by BioInteractions, Ltd., U.K., under the brand name Evolve™. This coating derives its efficacy from a biguanide, and also is engineered to deliver the drug heparin. Further, Specialty Coating Systems, Indianapolis, IN, has disclosed the occlusion of known antimicrobial agents in a parylene film by vapor phase deposition polymerization, (see e.g. Kumar, et al., U.S. Pat. No. 9,210,933).

Proper cleaning and disinfecting of medical equipment in hospitals requires training. Proper cleaning and disinfecting of home medical equipment, such as a CPAP machine and its parts, relies on the home patient to follow cleaning and disinfecting instructions for their machine. For example, many CPAP machine suppliers provide a quaternary disinfectant product to dilute and disinfect the various components of a CPAP device. However, disinfection of the components is based entirely on a lay person's compliance, and thus when compliance is lacking, pathogens can take up residence in the device and infect the user of the device.

Notwithstanding these and other achievements in the field of medical device coatings, new antimicrobial coatings and methods are always needed. In particular, new antimicrobial coatings that can be applied to medical implements that will undergo autoclaving prior to use, and coatings applicable to plastic parts used in catheters and CPAP and biPAP machines are still needed.

SUMMARY

It has now been discovered that under the proper application conditions, certain organosilane compositions find use in providing antimicrobial coatings on both medical implements and medical devices. Residual antimicrobial coatings on medical implements have been found to survive autoclaving. In various examples, residual antimicrobial coatings on various components of CPAP/biPAP and other devices ensure safety for the user of this equipment. Residual antimicrobial coatings on medical devices and equipment may be purposely designed to be permanent or dissolving, such as to fit a particular need, and to address the issues associated with the device or equipment or the medical procedures for their use. In various embodiments, antimicrobial coatings on an implantable device, such as a stent, changes the hydrophilicity/hydrophobicity of the surfaces and consequently affects the fluid dynamics around the implant in the vessel it's implanted in.

In various embodiments, antimicrobial coating compositions for use in coating medical implements and medical devices comprise at least one organosilane $(R^1O)_3Si-R^2-Z$, wherein $R^1$ is H, alkyl, substituted alkyl, aryl or substituted aryl, $R^2$ is a bivalent linker, and Z is a nucleophile, leaving group, or quaternary nitrogen substituent.

In various embodiments, the medical device is selected from the group consisting of coronary stents, artificial joints, components of artificial joints, pins, bone screws, prosthetic limbs, prosthetic breasts, prosthetic eyes, artificial heart valves, artificial vessels, mechanical hearts, pacemakers, support screens, staples, electrical wires, electrodes, sensors, CPAP machines, CPAP machine parts, biPAP machines, and biPAP machine parts.

In various embodiments, the medical implement is selected from the groups consisting of scalpels, clamps, forceps, retractors, distractors, drill bits, trocars, scissors, dilators, specula, intravenous (IV) catheters, urinary catheters, colostomy bags, endoscopes, probes, cryotomes, tubing, connectors, valves, syringes, needles, trays, IV stands, and bedrails.

In various embodiments, $R^2$ is $-CH_2CH_2CH_2-$.

In various embodiments, Z is $-NH_2$, a halogen, $-N(CH_3)_3{}^+X^-$, or $-N(CH_3)_2(n-C_{18}H_{37})^+X^-$, wherein $X^-$ is chloride, bromide, iodide, or bitartrate.

In various embodiments, the antimicrobial coating composition further comprises an organic amine of formula $R^9R^{10}R^{11}N$, wherein $R^9$, $R^{10}$, and $R^{11}$ are independently H, alkyl, substituted alkyl, aryl, substituted aryl or cyclic.

In various embodiments, Z is halogen and the organic amine is diethanolamine or triethanolamine, or mixtures thereof.

In various embodiments, the antimicrobial coating composition further comprises a Ti(IV) species selected from the group consisting of $TiO_2$, $Ti(OR^3)_4$, $Ti-(O\text{-}i\text{-}C_3H_7)_4$, $TiCl_4$ or a mixture of peroxotitanium acid and peroxo-modified anatase sol, wherein each $R^3$ is independently alkyl, substituted alkyl, aryl, or substituted aryl. In various embodiments, antimicrobial coating compositions for use in coating medical devices and implements comprise the reaction product between a titanium (IV) oxide of formula $Ti(OR^3)_4$ wherein each $R^3$ is alkyl, substituted alkyl, aryl, or substituted aryl, and a 1,2-diol, α-hydroxy acid, or β-hydroxy acid.

In various embodiments, a medical device or medical implement comprises: a metal or silicone rubber surface; and an antimicrobial coating composition dried on the surface, the antimicrobial coating composition comprising: (i) at least one organosilane $(R^1O)_3Si-R^2-Z$; and (ii) at least one amine $R^9R^{10}R^{11}N$, wherein $R^1$ is H, alkyl, substituted alkyl, aryl or substituted aryl, $R^2$ is a bivalent linker, Z is a nucleophile, leaving group, or quaternary nitrogen substituent, and $R^9$, $R^{10}$, and $R^{11}$ are independently H, alkyl, substituted alkyl, aryl, substituted aryl or cyclic; and wherein the medical device or medical implement exhibits residual antimicrobial efficacy against at least one of S. epidermidis or E. aerogenes.

In various embodiments, the at least one organosilane consists essentially of a mixture of octadecyldimethyl-(3-trimethoxysilylpropyl) ammonium chloride and 3-chloropropyltrimethoxysilane, and the at least one amine is triethanolamine.

In various embodiments, the at least one organosilane consists essentially of 3-aminopropyltriethoxysilane, and the at least one amine is triethanolamine.

In various embodiments, the metal surface comprises Nitinol or stainless steel.

In various embodiments, a method of coating a medical device or medical implement, the method comprises: immersing the medical device or medical implement in an aqueous composition comprising at least one organosilane $(R^1O)_3Si-R^2-Z$ and at least one amine $R^9R^{10}R^{11}N$; drying the medical device or medical implement; and optionally autoclaving the medical device or medical implement to produce the coated medical device or medical implement, wherein $R^1$ is H, alkyl, substituted alkyl, aryl or substituted aryl, $R^2$ is a bivalent linker, Z is a nucleophile, leaving group, or quaternary nitrogen substituent, and $R^9$, $R^{10}$, and $R^{11}$ are independently H, alkyl, substituted alkyl, aryl, substituted aryl or cyclic; and wherein the coated medical device or medical implement exhibits residual antimicrobial efficacy against at least one of S. epidermidis or E. aerogenes.

In various embodiments, the medical device or medical implement comprises Nitinol, silicone rubber or stainless steel.

In various embodiments, $R^2$ is $-CH_2CH_2CH_2-$ and Z is $-NH_2$, a halogen, $-N(CH_3)_3{}^+X^-$, or $-N(CH_3)_2(n\text{-}C_{18}H_{37})^+X^-$, wherein $X^-$ is chloride, bromide, iodide, or bitartrate.

In various embodiments, the at least one organosilane consists essentially of a mixture of octadecyldimethyl-(3-trimethoxysilylpropyl) ammonium chloride and 3-chloropropyltrimethoxysilane, and the at least one amine is triethanolamine.

In various embodiments, the at least one organosilane consists essentially of 3-aminopropyltriethoxysilane, and the at least one amine is triethanolamine.

In various embodiments, the medical implement is allowed to dry under ambient conditions and then is autoclaved for 20 minutes at 121° C. after the ambient drying.

In various embodiments, a method of providing a residual antimicrobial coating on a portion of a surface of a CPAP or BiPAP machine component comprises: immersing the portion in an aqueous composition comprising at least one organosilane $(R^1O)_3Si-R^2-Z$ and at least one amine $R^9R^{10}R^{11}N$; drying the portion under ambient conditions; and thermally curing the portion, wherein $R^1$ is H, alkyl, substituted alkyl, aryl or substituted aryl, $R^2$ is a bivalent linker, Z is a nucleophile, leaving group, or quaternary nitrogen substituent, and $R^9$, $R^{10}$, and $R^{11}$ are independently H, alkyl, substituted alkyl, aryl, substituted aryl or cyclic; and wherein the portion exhibits residual antimicrobial efficacy against at least one of S. epidermidis or E. aerogenes.

In various embodiments, the surface of the component of the CPAP or biPAP machine comprises silicone rubber.

In various examples, a method of forming a residual antimicrobial coating on a medical implement or medical device includes any number, type and combination of curing steps, including ambient drying, thermal treatment at elevated temperature and autoclaving.

In various embodiments, multiple antimicrobial coating compositions are used in various combinations and application sequences to provide residual antimicrobial coatings on medical implements and medical devices, including the components of medical equipment.

DETAILED DESCRIPTION

The detailed description of exemplary embodiments herein makes reference to the accompanying drawings, which show exemplary embodiments by way of illustration and their best mode. While these exemplary embodiments are described in sufficient detail to enable those skilled in the art to practice the disclosure, it should be understood that other embodiments may be realized and that logical, chemical, and mechanical changes may be made without departing from the spirit and scope of the disclosures. Thus, the detailed description herein is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Antimicrobial coating compositions are disclosed. In various embodiments, antimicrobial coating compositions comprise at least one of an organosilane, a titanium (IV) species, and a parylene polymer, in any combination. Antimicrobial coating compositions provide residual antimicrobial coatings on medical implements, components of medical equipment, and implantable and non-implantable medical devices when applied thereon. In various embodiments, coatings for use in various embodiments are useful on medical implements that are autoclaved. In various embodiments, antimicrobial coatings on implantable devices are engineered to dissolve off from the device with one to a few days time to provide protection against post-surgical implant infections. In other embodiments, antimicrobial coatings on implantable devices are engineered to be permanent.

As used herein, the term "organosilane" refers to silicon-containing organic chemicals, as opposed to inorganic forms of silicon, such as $SiO_2$ and water glass species ($Na_2SiO_3$, and the like). An organosilane is typically a molecule including carbon and silicon atoms, but may also include any other heteroatoms such as oxygen, nitrogen, or sulfur. Organosilane compounds for use in various embodiments may be chemical reactive or inert, and may be monomeric, dimeric, trimeric, tetrameric, or polymeric. Organosilane monomers for use in various embodiments may be chemically reactive in that they at least partially hydrolyze or polymerize, or form various adducts and/or polymers with other chemical species. Exemplary organosilanes for use in various embodiments include, but are not limited to, organosilanes having three reactive groups on silicon and one non-hydrolyzable group, such as for example, 3-chloropropyltrialkoxysilane and 3-aminopropyltrialkoxysilane, and adducts, hydrolysis products, self-condensation products, and polymeric reaction products therefrom.

As used herein, the term "titanium (IV) species" refers to any chemical compound comprising at least one tetravalent titanium atom, regardless if monomeric, dimeric, trimeric, or polymeric. Non-limiting examples include titanium (IV) oxide ($TiO_2$) in any form, other Ti(IV) species, (e.g., $TiCl_4$, Ti—(O-i-$C_3H_7$)$_4$ or any other Ti(IV) alkoxide, phenoxide or halide). Various forms of $TiO_2$ for use herein include, but are not limited to, rutile, anatase, brookite, hollandite-like, ramsdellite-like, $\alpha$-$PbO_2$-like, baddeleyite-like form, orthorhombic $TiO_2$—OI, cubic, and/or cotunnite-like forms. The most common crystalline forms are anatase, brookite and rutile. In various examples, Ti(IV) species for use herein comprise Ti nanoparticles. Further, Ti(IV) species for use herein include "titanyl-oxide moieties," which is a broad term defined herein to include any and all Ti compounds and mixtures known to form $TiO_2$ thin films, or at least suspected as able to form $TiO_2$ thin films, such as via the sol-gel process. A titanyl sol-gel is a precursor in the preparation of $TiO_2$ thin films. For example, a mixture of Ti(OC$_4$H$_9$)$_4$, ethanol, water, and diethanolamine, in a 1:26.5:1:1 molar ratio, has been disclosed as forming a $TiO_2$ film (see J. Yu et al., *Materials Chemistry and Physics*, vol. 69, pp 25-29 (2001)). This reference further discloses that whether or not the film is photocatalytic depends, inter alia, on the curing conditions for the sol-gel after surface application, e.g. using high temperatures. In another non-limiting example, a sol-gel route to mesoporous and nanocrystalline anatase thin layers begins with acidic hydrolysis of titanium isopropoxide, (see F. Bosc, *Chem. Mater.*, 15(12), pp 2463-2468, (2003)).

In certain examples, titanyl-oxide moieties for use herein comprise a colloidal suspension of from about 0.5 wt. % to about 50 wt. % $TiO_2$ in water. In other examples, titanyl-oxide moieties comprise an aqueous mixture of Ti—(O-i-$C_3H_7$)$_4$ usable to create a thin film of $TiO_2$ via the sol-gel process. Such compositions may also comprise an organic solvent, such as an alcohol like n-propanol or n-butanol, a surfactant, or an acid catalyst. In the sol-gel process, $TiO_2$ is prepared by hydrolysis, condensation and polycondensation of a titanium alkoxide, such as Ti—(O-i-$C_3H_7$)$_4$ or $TiCl_4$. A $TiO_2$ sol-gel composition, when coated onto a portion of a surface, provides a thin film $TiO_2$ coating on the portion of the surface.

In various embodiments, titanyl-oxide moieties comprise Ti(OR$^3$)$_4$, wherein R$^3$ is alkyl, substituted alkyl, aryl, or substituted aryl, and wherein the four separate R$^3$ groups are identical or different. Examples of Ti(OR$^3$)$_4$ include, but are not limited to, titanium tetramethoxide, titanium tetraethoxide, titanium methoxide triethoxide, titanium tetra-n-propoxide, titanium tetra-i-propoxide, and titanium tetraphenoxide. Depending on the physical properties of the titanium (IV) species, the compound may be used neat (e.g. Ti—(O-i-$C_3H_7$)$_4$) or dissolved in an alcohol or other organic solvent(s), such as the corresponding alcohol, where feasible, (methanol, ethanol, i-propanol, etc.). Thus, titanyl-oxide moieties may in some instances comprise a solution of Ti—(O-i-$C_3H_7$)$_4$ in isopropanol or some other alcohol.

In various embodiments, titanyl-oxide moieties comprise Ti(OR$^3$)$_4$, wherein R$^3$ is alkyl, substituted alkyl, aryl, or substituted aryl. In certain aspects, titanyl-oxide moieties may further comprise a solvent selected from the group consisting of water, alkanols, diols, triols, chlorinated organic solvents, ethers, amines, esters, ketones, aldehydes, lactones, phenolics, and mixtures thereof. In certain examples, a solvent is selected from, but not limited to, water, methanol, ethanol, n-propanol, i-propanol, ethylene glycol, 1,2-propanediol, 1,3-propanediol, glycerin, methylene chloride, trichloromethane, carbon tetrachloride, ethylene glycol monoalkyl ether, ethylene glycol dialkylether, propylene glycol monoalkyl ether, propylene glycol dialkyl ether, ethylene glycol monophenyl ether, ethylene glycol diphenyl ether, propylene glycol monophenyl ether, propylene glycol diphenyl ether, diethylether, tetrahydrofuran, pyridine, triethanolamine, diethanolamine, triethylamine, ethylacetate, acetone, furfural, and N-methyl-2-pyrrolidone, and combinations thereof. In various examples, titanyl-oxide moieties consist essentially of Ti—(O-i-$C_3H_7$)$_4$. Other examples include Ti—(O-i-$C_3H_7$)$_4$ and an alcohol, and a composition comprising Ti—(O-i-$C_3H_7$)$_4$ and isopropanol.

In various examples, titanyl-oxide moieties for use herein comprise an aqueous solution of peroxotitanium acid and peroxo-modified anatase sol, which is disclosed in the literature as a room temperature route to $TiO_2$ thin films, (see Ichinose, H., et al., *Journal of Sol-Gel Science and Technology*, September 2001, Volume 22, Issue 1-2, pp 33-40, and Ichinose, H., et al., *J. Ceramic Soc.* Japan, Volume 104, Issue 8, pp 715-718 (1996)).

In various examples, the titanyl-oxide moieties for use herein is a sol-gel that comprises about 0.5 wt. % peroxotitanium acid and about 0.5 wt. % peroxo-modified anatase sol, remainder water. A non-limiting example of a titanyl-oxide moieties composition for use herein comprises 0.85 wt. % of a mixture of peroxotitanium acid and peroxo-modified anatase sol (titanium oxide (IV)), remainder water. In various examples, a titanyl-oxides moieties composition comprises 0.8-0.9 wt. % of a mixture of titanium oxide (IV) and peroxotitanium acid, with the remainder, i.e., 99.1-99.2 wt. %, water. In various embodiments, this sol-gel mixture may be referred to as "0.85 wt. % aqueous peroxotitanium acid and peroxo-modified anatase sol."

Titanium (IV) species for use in various coating processes may be white or transparent, and may be photocatalytic or not. A titanium (IV) species, including the group of titanyl-oxide moieties discussed above, may be cast onto hard or pliable (plastic/rubber) surfaces to produce an antimicrobial coating, or used as a bonding agent to bond other substances, such as organosilanes, to hard or pliable surfaces to form more durable antimicrobial coatings on medical devices and medical implements. In some instances, a titanium(IV) species may be used in conjunction with an organosilane to "regulate" the durability of the antimicrobial coating. In other words, varying amounts and types of titanium (IV) species modulate the rate at which an organosilane may dissolve off from a medical device or implement. In some instances, a titanium(IV) species is not used at all in the coatings for a medical device such as a component for a hip or knee replacement, in which case an antimicrobial silane coating may intentionally dissolve off the implant and into the surrounding tissue in the day or so following surgery to help mitigate post-surgery infection and complications.

As used herein, the term "adduct" refers to a chemical combination of two or more chemical species, regardless of what forces hold the particular combination together. For example, two chemical species may form an adduct that comprises an ionic or covalent bond between the species, or even van der Waals or hydrogen bonds. A non-limiting example is the adduct $(MeO)_3Si-CH_2CH_2CH_2-N(CH_2CH_2OH)_3^+Cl^-$ resulting from the reaction, under certain conditions, between 3-chloropropyltrimethoxysilane and triethanolamine. Another non-limiting adduct is the hydrogen bonded chelate resulting from the association between triethanolamine and 3-aminopropyltrimethoxysilane, wherein the $-OH$ groups of the triethanolamine are hydrogen bonded to the $-NH_2$ group of the organosilane. Adducts for use in various embodiments do not need to comprise an organosilane, as they may be formed, for example, from the combination of other molecular species. A non-limiting example of such an adduct not comprising silicon is the compound resulting from reaction of a titanium (IV) species such as $Ti-(O-i-C_3H_7)_4$ and a diol.

As used herein, the term "polymer" takes on its ordinary meaning, which is at least two monomer species linked together to form any larger molecular weight compound. For the sake of simplicity, a polymer includes at least four monomers so as to distinguish from a dimer, trimer and tetramer. Thus, as few as five monomers covalently linked together comprise a polymer for purposes for use in various embodiments. In accordance with the ordinary meaning, a polymer may include any combination of any monomeric species, and may be linear, branched or other configuration (e.g. dendritic). Further, a polymer may be organized as a homopolymer of one monomer or any type of co-polymer having more than one monomeric species (block, random, etc.). A polymer may have a recognizable repeating structure, such as having a defined backbone, or may have branched and random structure with multiple sets of repeating units or a structure that cannot be easily described due to the randomness. Polymers for use in various embodiments may have undefined molecular size and structure. In instances wherein complete structural elucidation is not possible, polymers may be denoted as having n repeating units, wherein n=1 to infinity. In various embodiments, polymers may also comprise adducts. One such non-limiting example is a grafted polymer formed by derivatization of a parylene polymer with an organosilane.

As used herein, the term "parylene" refers to the broad genus of (poly)-p-xylylene polymers, with the general formula $-[CH_2-C_6H_4-CH_2]_n-$ representing the unsubstituted polymer referred to as parylene-N. The phenyl ring of the p-xylylene group may be substituted, such as with one chlorine atom (parylene-C), $-[CH_2-C_6H_3Cl-CH_2]_n-$, or two chlorine atoms, (parylene-D), $-[CH_2-C_6H_2Cl_2-CH_2]_n-$. In various embodiments, parylene polymers are grafted with organosilane chains, such as to form parylene polymers having a $-CH_2CH_2CH_2-Si(OR^1)_3$ substituent on each one of the p-xylylene repeating groups.

As used herein, the term "alkyl" refers to any linear, branched or cyclic monovalent carbon containing radical, such as, for example, methyl, ethyl, n-propyl, i-propyl, n-butyl, i-butyl, t-butyl, cyclopropyl, cyclohexyl, and the like. A "substituted alkyl" substituent refers to the above alkyl group that also bears at least one other group including a heteroatom, such as an $-OH$, $-SH$, $-OCH_3$ or $-CO_2H$ substituent, or at least one intervening atom positioned in the carbon chain of the alkyl group. Thus, a substituted alkyl group may include such monovalent species as $-CH_2-O-CH_3$, and $-CH_2CH_2-N(CH_3)-CH_2CH_3$. Since alkyl groups may be cyclic, "substituted alkyl group" also encompasses all non-aromatic heterocyclic species. A non-limiting example of the latter is a 1-morpholinyl substituent.

When referring to at least two substituents "R" bonded to a common atom, such as $R^9R^{10}R^{11}N$, the option of "cyclic" refers to the situation wherein at least two of the "R" substituents form a ring structure that includes the common atom to which the "R" groups are bonded. Thus, as an example, the genus structure $R^9R^{10}R^{11}N$, wherein $R^9$, $R^{10}$, and $R^{11}$ are alkyl, includes N-methylpyrrolidine, amongst many other chemical species.

As used herein, the term "aryl" takes on the ordinary meaning of an aromatic substituent, including phenyl and any heteroaryl, e.g. pyridyl, imidazoyl, and the like. A "substituted aryl" refers to a substituted phenyl group or a substituted heteroaryl moiety, wherein the substitution is in any position around the aromatic ring, and in any combination.

As used herein, the term "nucleophile" takes on the ordinary meaning in organic chemistry, which refers to a substituent capable of donating an electron pair to an electrophilic species to form a chemical bond. Examples of neutral substituents that would be considered nucleophilic substituents attached to a chemical species include, but are not limited to, $-OH$, $-SH$, $-NH_2$, $-NHR^8$, and $-NR^9R^{10}$. Thus, a molecular species such as $R-OH$ is considered nucleophilic because it contains the nucleophilic hydroxyl substituent $-OH$. Anionic substituents are also considered nucleophilic. Examples include, but are not limited to, $-O^-$, $-S^-$, $-CO_2^-$, and the like.

As used herein, the term "leaving group" takes on the ordinary meaning in the field of organic chemistry, which refers to a molecular fragment or substituent that departs from a molecular species with a pair of electrons upon heterolytic bond cleavage. Chemical reactions for use in various embodiments may comprise the reaction between a nucleophile and an electrophilic atom having a leaving group attached thereto, which results in a new bond formed between the nucleophile and the electrophilic atom and the departing of the leaving group (i.e. an SN2-type reaction). As examples for use in various embodiments, an amine (nucleophile) may displace a halogen (leaving group) from a carbon atom resulting in a new C—N bond and the expulsion of the halogen, or a tertiary amine (nucleophile) may displace a halogen (leaving group) from a carbon atom resulting in a new quaternary ammonium compound having C bonded to a positively charged N that has three other appendages (i.e. quaternary). In this case, the halogen is the negatively charged counterion to the quaternary/positively charged N.

As used herein, the term "medical implement" refers to any and all medical tools, devices, and equipment used outside the patient's body. For sake convenience, the term is extended herein to include catheters and needle assemblies and other implements that are partly and/or temporarily inserted into a patient. Examples of medical implements include, but are not limited to, scalpels, clamps, forceps, retractors, distractors, drill bits, trocars, scissors, dilators, specula, intravenous (IV) catheters, urinary catheters, colostomy bags, endoscopes, probes, cryotomes, various vinyl, plastic and rubber tubing, connectors, valves, syringes, needles, trays, IV stands, bedrails, and the like. Medical implements may or may not be autoclaved prior to use on a patient or in the treatment room with the patient. In various embodiments, a medical implement may be sterilized or disinfected by other means other than autoclaving prior to use, (e.g. by ozone or UV radiation). Medical implements may comprise any type of material, such as stainless steel (e.g. 305, 316 stainless), chromium, nickel, or titanium, or any other metal or metal alloy, silicone or other rubber, elastomeric polymer, natural polymer, glass, or any type of plastic. A non-limiting specific example of a medical implement is a 316 stainless steel surgical clamp, which more likely than not, will be autoclaved prior to use. Other medical implements, such as urinary catheters, may be made of high consistency rubber (HCR) that comprises millable thermoset silicone elastomers.

As used herein, the term "medical device" refers to any and all devices and components of devices used in the medical field, including but not limited to, implantable structures, which may attach onto a patient or may be embedded inside a patient permanently or temporarily, and medical equipment, including for example, home health monitoring equipment (stethoscope, blood pressure cuff, and the like) and breathing apparatuses such as CPAP or biPAP machine, and all of the components and accessories thereof.

Implantable devices may comprise any metal or non-metal material, or combinations thereof, and may be designed to be temporarily or permanently implanted. Examples of medical devices include, but are not limited to, coronary stents, artificial joints, pins, bone screws, prosthetic limbs, prosthetic breasts, prosthetic eyes, artificial heart valves, artificial vessels, mechanical hearts, pacemakers, support screens, staples, electrical wires, sensors, electrodes, and the like. Medical devices may comprise any type of material, such as stainless steel, cobalt, chromium, nickel, lithium, or titanium, or any other single metal or metal alloy, any silicone or other rubber, elastomeric polymers, natural polymers, glass, or any type of plastic. Stents may have any shape and configuration, such as tubular or branched, with various struts and linkages to allow compression inside a catheter and/or expansion within a vessel. A non-limiting specific example of a medical device is a CoCr alloy shape memory coronary stent. Implantable devices may be designed to dissolve and eventually disappear, (e.g. corroding stents of an iron alloy, or staples or sutures used for temporary fastening), or may be designed to be permanent fixtures (e.g., a titanium and plastic artificial hip joint) lasting the life of the patient. Medical devices such as these may be coated in accordance to the present disclosure, and the medical device may maintain antimicrobial efficacy on its surface throughout the lifetime of the device or the patient. In various examples, coatings on implanted medical devices maintain stability and antimicrobial efficacy in the constant presence of physiological fluid, such as blood or synovial fluid.

In various embodiments, antimicrobial coatings on medical devices are designed not to be permanent. Rather, antimicrobial coatings may simply dissolve away as the implant, such as a dissolvable stent or a staple, corrodes and dissolves away. In more specific examples, such as antimicrobial coatings on titanium or Ni—Ti components of artificial hips and knees, an antimicrobial coating can be engineered to dissolve away from the implant once implanted in a patient, in from about 1-day to about 7-days, to provide antimicrobial efficacy in the tissue surrounding the implant. In this way, post-surgical infections are mitigated by the dissolving antimicrobial coating over the period of time most susceptible to infection. Once the implant is stable, the antimicrobial coating on the implant is no longer needed and is no longer present.

In specific examples, medical devices that may be coated with the antimicrobial coating compositions of the present disclosure include coronary stents. One of the more common self-expanding stents is the Nitinol stent, which is a metal stent constructed of a NiTi alloy having shape memory properties. Other coronary stents include those made of stainless steel, NiCr, PtCr, or CoCr alloys. Coronary stents may be drug eluting or "bare." An example of the latter is the Coroflex Blue Neo CoCr coronary stent from B. Braun. For purposes for use in various embodiments, stents or other medical device may be first coated with one or more antimicrobial coating compositions followed by a drug coating, or the other way around.

In other embodiment, medical devices that may be coated with the antimicrobial coating compositions of the present disclosure include artificial joints such as artificial hips, including any one of the components therein. Hip implants usually comprise a minimum of a ball or femoral head, a cup or pinnacle acetabular shell, cup liner or insert, and a femoral stem, although partial implants or hip resurfacing procedures may only use one or some of these components rather than all for a complete hip replacement joint. The materials of construction for the components of a hip joint vary widely, and depend on the component, and may include such materials as polyethylene or ultra-high molecular weigh polyethylene (UHMWPE), or ultra-highly cross-linked polyethylene (UHXLPE), various ceramic materials, and metal alloys such as CoCr or a Ti alloy. Complete hips may be metal-on-plastic or metal-on-metal. In accordance to the present disclosure, antimicrobial coating compositions are applied to the various components of artificial joints such as hip joints to form residual antimicrobial coatings on the components of the artificial joint. Other artificial joints such as knee and shoulder joints have similar component structure, any of which may be coated with the antimicrobial coating compositions of the present disclosure to form residual antimicrobial coatings on those components. For example, an artificial knee joint generally includes a femoral component, a plastic spacer and a tibial component. The latter may vary as to fixed-bearing or mobile-bearing. In shoulder prostheses, there is generally the head of the humerus bone (referred to as the ball) and the glenoid (the socket).

Medical devices that may be coated with the antimicrobial coating compositions of the present disclosure include CPAP and biPAP machines and their components and accessories. CPAP stands for "continuous positive airway pressure," and thus the device is designed to deliver such and is used to assist breathing and most particularly to treat obstructive sleep apnea. The person in need of treatment wears a face mask while sleeping and the CPAP machine forces air into the nose of the patient to overcome obstructions. The air may be moisturized, such as by a humidifier module built into the CPAP machine. BiPAP stands for "bilevel positive airway pressure," and is very similar to CPAP. However, CPAP can only deliver air at the single pressure it is set to deliver, whereas biPAP, with two pressure settings, can temporarily increase pressure to the higher setting to force the patient to breathe. Herein, CPAP refers to both CPAP and biPAP since the components (face masks, hoses, etc.) are generally the same.

In various aspects, components of a CPAP machine may be coated with the antimicrobial coating composition of the present disclosure by the manufacturer or distributor, or in some cases, may be coated by health care professional or even the home user from time to time. In the latter scenario, a user of a CPAP machine may wish to treat their own components at home with the antimicrobial coating compositions herein, such as to "refresh" surfaces and impart residual antimicrobial properties to the surfaces.

As used herein, the term "antimicrobial" is used generally to indicate at least some degree of microbe kill or mitigation of microbe reproduction by an antimicrobial composition or a residual antimicrobial coating disposed on a soft surface. For example, the term antimicrobial may be used to indicate a bacteriostatic effect, a sanitizing level (3-log, or 99.9%) of reduction in at least one organism, a disinfection level (5-log, or 99.999%) of reduction in at least one organism, or complete sterilization (i.e., no detectable organisms). Microbes, or microorganisms, may include any species of bacteria, virus, mold, yeast, or spore.

The terms "residual antimicrobial," "residual self-sanitizing," and "self-decontaminating surface" are used interchangeably to indicate a hard or soft surface that maintains antimicrobial efficacy over a certain period of time under certain conditions once the surface is coated with an antimicrobial coating composition. A coated surface may maintain residual antimicrobial efficacy indefinitely, or the coating may eventually "wear out" and lose its residual antimicrobial efficacy. An antimicrobial coating composition may function as a contact sanitizer, disinfectant, or sterilant, (e.g. as a liquid antimicrobial applied to a contaminated surface) and also have the ability to leave behind a residual antimicrobial coating on the surface once dried or cured thereon that can keep inactivating new microorganisms that contact the coated surface. In various embodiments, coating compositions may not be antimicrobial until dried or cured on a surface, but are still referred to as antimicrobial coating compositions because of their ability to produce a residual antimicrobial coating on a surface. Antimicrobial coating compositions for use in various embodiments may provide a residual antimicrobial efficacy to a surface of a medical implement or medical device, meaning that a microorganism later inoculated on or that otherwise comes in contact with the coated surface may experience cell death, destruction, or inactivation. The residual antimicrobial effect made possible by the coatings is not limited by a particular mechanism of action, and no such theories are proffered. For example, an antimicrobial effect measured on a surface may be the result of intracellular mutations, inhibition of certain cellular processes, rupture of a cell wall, or a nondescript inactivation of the organism. Other antimicrobial effects may include inhibiting the reproduction of an organism, or inhibiting the organism's ability to accumulate into biofilms.

As used herein, the term "antimicrobial coating composition" refers to a chemical composition comprising at least one chemical species, which is used to produce a residual antimicrobial coating on a medical device or medical implement after the composition is applied and then either manually dried, passively allowed to dry, thermally treated and/or autoclaved. However, the term is extended to include a composition that may be applied in a coating sequence (e.g. over or under) or contemporaneously with the application of an antimicrobial coating composition comprising an antimicrobial active, such as to assist in bonding the residual antimicrobial coating to the surface, improve longevity of the overall coating, and/or to provide a catalytic effect or some sort of potentiation or synergy with the residual antimicrobial coating comprising an antimicrobial active. For simplicity, each one of multiple compositions used sequentially or contemporaneously to produce an overall residual antimicrobial coating on a medical dressing is referred to as an "antimicrobial coating composition," regardless if one or more of the compositions used in the coating process has no identifiable antimicrobial active, or where the active agent is uncertain. An antimicrobial coating composition may comprise a neat, 100% active chemical species or may be a solution or suspension of a single chemical species in a solvent. In other aspects, a composition may comprise a complex mixture of chemical substances, some of which may chemically react (hydrolyze, self-condense, etc.) within the composition to produce identifiable or unidentifiable reaction products. For example, a monomeric chemical species in an antimicrobial coating composition may partially or fully polymerize while in solution prior to a coating process using that composition. In various embodiments, chemical constituents within an antimicrobial coating composition may chemically react on the plastics, metals or other materials of the medical devices or implements that the composition is applied to, such as while the composition is drying and concentrating on the surfaces or while the coating composition is cured by various methods on the surfaces. In various examples, the surfaces themselves may have certain catalytic effect, such as simple pH effects, which may promote certain chemical reactions and bonding to occur. Antimicrobial coating compositions may further comprise any number and combination of inert excipients, such as for example, solvents, surfactants, emulsifiers, stabilizers, thickeners, free-radical initiators, catalysts, pH adjustors, etc. In various examples, antimicrobial coating compositions disclosed herein include an indicator, such as a dye, that aids in determining coating thickness, uniformity, coverage, durability, presence, and the like. Such an indicator may turn from colorless to colored, or vice versa, when an antimicrobial coating on a medical device or medical implement is no longer present or has become ineffective.

An antimicrobial coating composition herein is usable to form a dry residual antimicrobial coating on medical devices and medical implements once dried or cured thereon. Such a coating can keep inactivating new microorganisms that come in contact with the device or implement surfaces. In various embodiments, coating compositions may not become antimicrobial on the surfaces of the device or implements until dried or cured thereon, but are nonetheless, still referred to as antimicrobial coating compositions because of their ability to form a residual antimicrobial coating on a dressing. Antimicrobial coating compositions may provide a residual antimicrobial efficacy to medical devices and implements, meaning that a microorganism later inoculated on, or that otherwise comes in contact with, the coated surface of the device or implement may experience cell death, destruction, or inactivation, such as mitigated ability to reproduce to pathogenic levels. The residual antimicrobial effect made possible by the coatings herein is not limited by a particular mechanism of action, and no such theories are proffered. For example, an antimicrobial effect, such as measured by inoculating a treated surface of a medical device or implement, may be the result of intracellular mutations, inhibition of certain cellular processes, rupture of a cell wall, or a nondescript inactivation of the organism. Other antimicrobial effects may include inhibiting the reproduction of an organism, or inhibiting the organism's ability to accumulate into colonies or other agglomerations.

As used herein, the term "curing" includes all known curing methods in the chemical and engineering arts. These include, but are not limited to, ambient curing, radiation curing and chemical curing. For example, an antimicrobial coating composition applied to a medical implement or medical device may be subject to UV, visible light, microwave, ion beam or other incident radiation in order to cure the composition on the surface of the implement or device. Radiation curing also includes thermal radiation methods, (i.e. heat, or annealing), such as heating a coated medical implement or device in a convection oven, a vacuum oven, a furnace, or an autoclave. Thermal methods may include annealing a medical implement or device having an applied antimicrobial coating composition thereon to a temperature of from about ambient to about 1000° C. or higher, for a time sufficient to produce a residual antimicrobial coating on the implement or device. In other aspects, an antimicrobial coating composition may be applied to a medical implement or device and then the implement or device is allowed to dry at ambient conditions. Ambient conditions may include at least some control of the percent relative humidity (% RH). Curing by any of these methods may drive off volatile components such as solvents, and/or initiate and/or catalyze inter- or intra-molecular chemical reactions such as hydrolysis, inter- and intramolecular self-condensation, intermolecular polymerization between different species, or cross-linking of polymer chains, for example. During curing, such as ambient drying or annealing, a coating is developed on the surface of the medical implement or device that is durable to handling and other forms of wear and/or stable to physiological conditions such as blood flow for a desired period of time.

As used herein, the term "durable" refers to usable life of a coating under a prescribed condition. Thus, "durability" is not absolute, but is rather for a period of time under particular conditions. For example, a residual antimicrobial coating on a coronary stent may be deemed durable because it continues to deliver a log-3 (99.9%) reduction in E. coli for 6-months while submerged in circulating arterial plasma at 37° C., or perhaps the treated surfaces are resistant to accumulation of organisms, for example biofilm, for extended exposure times. For a durability assessment, a residual antimicrobial coating may be produced on a test coupon used as a surrogate for the medical implement or device. For example, to assess durability of a residual antimicrobial coating on a Nitinol stent, a Ni—Ti alloy coupon, such as cut from Nitinol sheet material, may be used. The coupon would then be immersed in simulated physiological fluid (e.g. simulated plasma) for an extended period of time to demonstrate durability. In other experiments, the treated coupon could be submerged in circulating inoculum to demonstrate the inhibition of bioaccumulation, such as biofilm. For medical implements, surrogate coupons may also be used. For example, to assess durability of a residual antimicrobial coating on a surgical clamp, a 316 stainless steel coupon may be used rather than the clamp itself. Various plastic test coupons are available that can be used to simulate non-metal medical implement surfaces. To assess durability to handling or "wear," EPA Protocol #01-1A, entitled "Protocol for Residual Self-Sanitizing Activity of Dried Chemical Residues on Hard, Non-Porous Surfaces," may be used. In this way, durability of a coating on, for example, a 316 stainless steel or a plastic coupon can be equated to the durability expected on a medical implement that is made of the same material and is frequently handled, such as during surgery.

In other examples, durability of an antimicrobial coating is characterized by the ability for a surface to retain at least biostatic antimicrobial efficacy over an extended period of time exposed to moist air. In these examples, antimicrobial surface may not be touched, handled or rubbed, but instead are subjected to air flow. A specific example of a durable antimicrobial coating on a medical device is residual bacteriostatic efficacy on the components of a CPAP or bi-PAP machine over an extended period of time exposed to flow of moist air. An even more specific example is the residual antimicrobial efficacy provided on the inside of a plastic hose and face mask used with a CPAP machine.

In various embodiments, durability may be nonexistent, or at least quite brief, such as in the cases where an antimicrobial coating on a medical device such as a component to a hip or knee replacement is designed to dissolve off in the surrounding tissue after the surgical implant.

In various embodiments, antimicrobial coating compositions are applied to medical implements and medical devices to produce a residual antimicrobial coating on the implement or the device or components of a device. In various embodiments, at least one coating composition is applied to an implement or device. The application process may comprise any single application method or a combination of application methods. In various examples, different application methods may be used for each of two or more successive coatings of antimicrobial coating compositions. In various embodiments, at least one coating is applied to an implement or a device, and in the instances where two or more coatings are applied, the coatings may be chemically the same or different. In various embodiments, any period of time may transpire between separate coatings of an implement or device, such as, seconds, minutes, hours, days, or longer. Medical implements may be recoated as necessary, such as between surgeries. Implanted medical devices may or may not be removed from the patient for recoating. Components of medical equipment may be recoated as necessary by a retailer, medical professional or even the end user at home.

In various embodiments, application methods include, but are not limited to, electroplating, electroless plating, chemical processes, anionic oxidation processes, dip/immersion coating, spray coating, electrostatic spray coating, vacuum plating, painting processes, surface hardening, and metallic cementation. Some of these categories are more useful for metal-based coatings, (e.g. titanium containing antimicrobial coating compositions, as discussed herein), while other categories are more useful for organic substances, (e.g. organosilanes and amines). For example, anionic oxidation processes are useful to create titanium oxide films by electrolysis of the implement or device made into an anode in an electrolytic solution. Painting processes, including spraying, electrostatic spraying, thermal spraying, brush coating, and electrodeposition painting, are also useful for applying an antimicrobial coating composition on the surface of a medical implement or medical device.

In various embodiments, a dip coating process is a simple and useful method for coating both medical implements and medical devices. For example, medical implements may be dipped into an antimicrobial coating composition and then placed directly into an autoclave. In this manner, the medical implement removed from the autoclave comprises a residual antimicrobial coating. In other embodiments, implements may sit in a tray filled with antimicrobial coating composition and removed when needed, air dried and then autoclaved or directly autoclaved. Medical implants such as expandable stents may be dip coated by immersion in an antimicrobial coating composition, and then allowed to dry, or oven dried. Such coated implants may then be coated with another antimicrobial coating compositions, such as by electrostatic spraying. Devices with complex structures, such as expandable vascular stents and abdominal/hernia support screens, may be effectively coated on all surfaces by dipping in a liquid composition or by electrostatic spray techniques.

In accordance to various embodiments, a residual antimicrobial coating on a medical implement or medical device may have unimolecular thickness (i.e., a monolayer), or may be macroscopically thick, such as having micron to millimeter thickness. In various embodiments, a residual antimicrobial coating is from about 1 nm to about 1 mm in thickness. In other examples, a residual antimicrobial coating is from about 1 nm to about 100 μm in thickness. Coatings may be flexible, durable, and resistant to flaking and chipping. Coatings of unimolecular thickness are not perceivable to the naked eye, and may be more resistant to flaking and chipping compared to coatings of macroscopic thicknesses.

Organosilane and Amine Coatings

In various embodiments, an antimicrobial coating composition comprises at least one organosilane of general structure $(R^1O)_3Si—R^2—Z$, or an adduct, hydrolysis product, or polymeric reaction product therefrom, wherein $R^1$ is H, alkyl, substituted alkyl, aryl, or substituted aryl, $R^2$ is a bivalent linker of any molecular chain length and comprises any degree of branching, which may comprise any number of methylene groups $—(CH_2)_n—$, optionally substituted with various substituents such as —OH, —SH, —OCH$_3$, or —CO$_2$H anywhere along the chain, and/or interrupted with intervening heteroatoms and/or degrees of unsaturation, and Z is a nucleophile, a leaving group or a quaternary nitrogen substituent.

An antimicrobial coating composition may further comprise a solvent, such as water and/or an alkanol, and/or any additional excipient such as, but not limited to, a surfactant, a quaternary salt, an inorganic silicate, an inorganic acid, and organic acid, an inorganic base or an organic base. In various examples, an organic base comprises any organic amine, such as diethanolamine or triethanolamine. In other examples, a quaternary salt comprises choline chloride or choline bitartrate.

In certain examples, an antimicrobial coating composition comprises at least one organosilane of general structure $(R^1O)_3Si—R^2—Z$, wherein $R^1$ is H, $CH_3$ or $CH_2CH_3$, $R^2$ is —CH$_2$CH$_2$CH$_2$—, and Z is —NR$^{12}$R$^{13}$, wherein $R^{12}$ and $R^{13}$ are independently H, alkyl, substituted alkyl, aryl, or substituted aryl. In other examples, Z is a halogen. In other more specific examples, $R^2$ is any bivalent linker, and Z is —NH$_2$, —N(CH$_3$)$_3^+$Cl$^-$, —N(CH$_3$)$_2$(n-C$_{18}$H$_{37}$)$^+$Cl$^-$, —OH, or —Cl. In another specific example, an antimicrobial coating composition comprises at least one organosilane of general structure $(R^1O)_3Si—R^2—Z$, wherein $R^1$ is H, $CH_3$ or $CH_2CH_3$, $R^2$ is —CH$_2$CH$_2$CH$_2$—, and Z is —NH$_2$. In yet another specific example, an antimicrobial coating composition comprises at least one organosilane of general structure $(R^1O)_3Si—R^2—Z$, wherein $R^1$ is H, $CH_3$ or $CH_2CH_3$, $R^2$ is —CH$_2$CH$_2$CH$_2$—, and Z is —Cl.

In various embodiments, an antimicrobial coating composition may comprise at least one of 3-chloropropyltrimethoxysilane, 3-chloropropyltriethoxysilane, 3-chloropropylsilanetriol, 3-aminopropyltrimethoxysilane, 3-aminopropyltriethoxysilane, 3-aminopropylsilanetriol, octadecyldimethyl-(3-trimethoxysilylpropyl) ammonium chloride (CAS No. 27668-52-6), or octadecyldimethyl-(3-trihydroxysilylpropyl) ammonium chloride (CAS No. 199111-50-7). It should be recognized that certain trialkoxysilanes hydrolyze in water at various rates of reaction to the corresponding trihydroxysilane species, which then may go on to self-polymerize into various oligomer distributions.

In various examples, an antimicrobial coating composition further comprises an organic amine. An organic amine for use in various embodiments may be primary, secondary, or tertiary in nature. In general, an organic amine for use in various embodiments may comprise an amine having structure $R^9R^{10}R^{11}N$, wherein $R^9$, $R^{10}$, and $R^{11}$ are independently H, alkyl, substituted alkyl, aryl, substituted aryl or cyclic. The latter option accentuates that an organic amine for use in various embodiments may be cyclic, (i.e. any two of $R^9$, $R^{10}$, and $R^{11}$ may form a ring with the N atom in the ring). Organic amines for use in various embodiments includes ammonia, ($R^9$, $R^{10}$, and $R^{11}$ are each H). In accordance to the general structure provided, an organic amine for use in various embodiments may comprise diethanolamine or triethanolamine, amongst many other species of amines.

In various examples, an antimicrobial coating composition comprises an organosilane of structure $(R^1O)_3Si—R^2—Z$, and at least one organic amine having structure $R^9R^{10}R^{11}N$, wherein $R^1$ is H, alkyl, substituted alkyl, aryl, or substituted aryl, $R^2$ is a bivalent linker Z is a nucleophile, a leaving group, or a quaternary nitrogen substituent, and $R^9$, $R^{10}$, and $R^{11}$ are independently H, alkyl, substituted alkyl, aryl, substituted aryl, or participate in forming a cyclic structure. Depending on the choices for these variables, there may be chemical reactions between the organosilane and the organic amine(s) in solution or on a surface, or no chemical reactions at all.

An antimicrobial coating composition may comprise at least one of 3-chloropropyltrimethoxysilane, 3-chloropropyltriethoxysilane, 3-chloropropylsilanetriol, 3-aminopropyltrimethoxysilane, 3-aminopropyltriethoxysilane, 3-aminopropylsilanetriol, octadecyldimethyl-(3-trimethoxysilylpropyl) ammonium chloride, or octadecyldimethyl-(3-trihydroxysilylpropyl) ammonium chloride, and at least one of diethanolamine or triethanolamine. An antimicrobial coating composition may further comprise any solvent such as water, any alkanol, or any mixture of solvents.

An antimicrobial coating composition may comprise at least one of 3-aminopropyltrimethoxysilane, 3-aminopropyltriethoxysilane, and 3-aminopropylsilanetriol, optionally with a choline salt such as choline chloride or choline bitartrate.

In various examples, an antimicrobial coating composition comprises an organosilane of structure $(R^1O)_3Si—R^2—Z$ that may undergo hydrolysis in solution. For example, an antimicrobial coating composition comprising 3-chloropropyltrimethoxysilane and water may also comprise 3-chloropropylsilanetriol and methanol. In certain embodiments, forming an antimicrobial coating composition comprising 3-chloropropyltrimethoxysilane in water results in an antimicrobial coating composition comprising 3-chloropropylsilanetriol, water, and methanol.

An antimicrobial coating composition comprising an organosilane of structure $(R^1O)_3Si—R^2—Z$ and optionally any other excipient such as an alkanol or amine, may be applied to a medical implement or medical device to form a residual antimicrobial coating on the implement or device. Any method of application may be used, such as spray or dip methods of coating. The treated implement or device may then be heated or exposed to radiation to cure the antimicrobial coating composition into a residual antimicrobial coating. Curing may comprise ambient drying, heated drying such as in an autoclave, or annealing.

In various embodiments, a residual antimicrobial coating on a medical implement or medical device comprises at least one organosilane of general structure $(R^1O)_3Si-R^2-Z$, or an adduct, hydrolysis product, or polymeric reaction product therefrom, wherein $R^1$ is H, alkyl, substituted alkyl, aryl, or substituted aryl, $R^2$ is a bivalent linker of any molecular chain length, which may comprise any number of methylene groups $-(CH_2)_n-$, optionally substituted with various substituents such as $-OH$, $-SH$, $-OCH_3$, or $-CO_2H$ anywhere along the chain, and/or interrupted with intervening heteroatoms and/or degrees of unsaturation, and Z is a nucleophile, a leaving group or a quaternary nitrogen substituent. In certain examples, a residual antimicrobial coating further comprises an organic amine having structure $R^9R^{10}R^{11}N$, wherein $R^9$, $R^{10}$, and $R^{11}$ are independently H, alkyl, substituted alkyl, aryl or substituted aryl.

A residual antimicrobial coating on a medical implement or medical device comprises a silsesquioxane of structure:

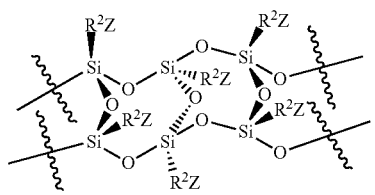

wherein $R^2$ is a bivalent linker of any molecular chain length, which may comprise any number of methylene groups $-(CH_2)_n-$, optionally substituted with various substituents such as $-OH$, $-SH$, $-OCH_3$, or $-CO_2H$ anywhere along the chain, and/or interrupted with intervening heteroatoms and/or degrees of unsaturation, and Z is a nucleophile, a leaving group or a quaternary nitrogen substituent.

A residual antimicrobial coating on a medical device or medical implement comprises an organosilane of structure $(R^1O)_3Si-R^2-Z$, wherein Z is a leaving group. In various examples, Z is $-Cl$. A residual antimicrobial coating comprises an organosilane of structure $(R^1O)_3Si-R^2-Z$, wherein Z is a halogen X, and a tertiary organic amine $R^9R^{10}R^{11}N$, wherein $R^9$, $R^{10}$, and $R^{11}$ are independently alkyl, substituted alkyl, aryl or substituted aryl.

In various embodiments, a residual antimicrobial coating on a medical device or medical implement comprises $(R^1O)_3Si-R^2-Z$, wherein $R^1$ is H, alkyl, substituted alkyl, aryl, or substituted aryl, $R^2$ is $-CH_2CH_2CH_2-$, and Z is $-Cl$. In certain examples, the residual antimicrobial coating further comprises an organic amine.

In various embodiments, a residual antimicrobial coating on a medical implement or medical device comprises $(R^1O)_3Si-R^2-Z$, wherein $R^1$ is H or alkyl, $R^2$ is $-CH_2CH_2CH_2-$, and Z is $-Cl$, and at least one of diethanolamine and triethanolamine.

In various embodiments, a residual antimicrobial coating on a medical implement or medical device comprises the adduct between $(R^1O)_3Si-R^2-Z$, wherein $R^1$ is H, alkyl, substituted alkyl, aryl, or substituted aryl, $R^2$ is a bivalent linker, and Z is a leaving group $-X$, and an amine of structure $R^9R^{10}R^{11}N$, wherein $R^9$, $R^{10}$, and $R^{11}$ are independently H, alkyl, substituted alkyl, aryl, substituted aryl, or cyclic, having the general structure:

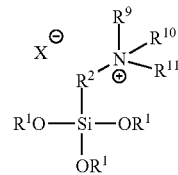

In various embodiments, $R^9$, $R^{10}$ and $R^{11}$ are each $-CH_2CH_2OH$, $R^2$ is any bivalent linker and X=halogen. In other examples, $R^9$ and $R^{10}$ are $-CH_3$, $R^{11}$ is -octadecyl, and X is Cl. In other examples, $R^9$, $R^{10}$ and $R^{11}$ are each $-CH_2CH_2OH$, $R^2$ is $-CH_2CH_2CH_2-$, X=Cl and $R^1$ is H or alkyl. In certain examples, $R^9$, $R^{10}$ and $R^{11}$ are each $-CH_2CH_2OH$, $R^2$ is $-CH_2CH_2CH_2-$, X=Cl, and $R^1$ is $-H$, $-CH_3$, or $-CH_2CH_3$. In certain examples, a residual antimicrobial coating comprises at least one of 3-(trimethoxysilyl)-propyldimethyloctadecyl ammonium chloride, 3-(trihydroxysilyl)-propyldimethyloctadecyl ammonium chloride, or polymers thereof, or mixtures thereof, optionally bonded to a surface. 3-(trimethoxysilyl)-propyldimethyloctadecyl ammonium chloride has at time been abbreviated as "Si-QAC," and herein abbreviated "DMOD." But it is important to recognize that other homologs of this quaternary silane exist that are antimicrobial, such as with other alkyl groups besides methyl and octadecyl groups. The surface bonded antimicrobial activity of the hydrolysis product from 3-(trimethoxysilyl)-propyldimethyloctadecyl ammonium chloride has been described in the academic literature, (see, for example, A. J. Isquith, et al., *Applied Microbiology*, 24(6), p 859-863, (1972)).

In various embodiments, a residual antimicrobial coating comprises the adduct between a choline salt and an organosilane $(R^1O)_3Si-R^2-Z$, wherein $R^1$ is H, alkyl, substituted alkyl, aryl, or substituted aryl, $R^2$ is a bivalent linker, and Z is a leaving group. The choline salt may comprise choline chloride, choline bitartrate, or any other choline salt. In specific embodiments, a residual antimicrobial coating comprises the adduct between $(R^1O)_3Si-R^2-Z$ and a choline salt, wherein $R^1$ is H, alkyl, substituted alkyl, aryl, or substituted aryl, $R^2$ is a is $-CH_2CH_2CH_2-$, and Z is a leaving group, with the adduct in the coating having the structure $(R^1O)_3Si-CH_2CH_2CH_2-O-CH_2CH_2-N(CH_3)_3{}^+X^-$, wherein $R^1$ is H, alkyl, substituted alkyl, aryl, or substituted aryl, and X is Z, the counterion from the starting choline salt, or a mixed salt.

In various embodiments, a residual antimicrobial coating on a medical implement or medical device comprises the adduct:

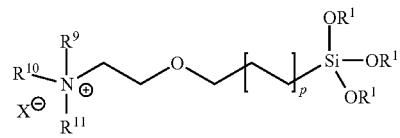

wherein $R^1$ is H, alkyl, substituted alkyl, aryl, or substituted aryl, $R^9$, $R^{10}$, and $R^{11}$ are independently H, alkyl, substituted alkyl, aryl, substituted aryl, or cyclic, X is selected from the group consisting of chlorine, bromine, iodine and bitartrate; and p is from 1 to 5.

In various embodiments, an antimicrobial coating formed from an antimicrobial coating composition comprising an organosilane $(R^1O)_3Si-R^2-Z$ and triethanolamine comprises the polymeric species:

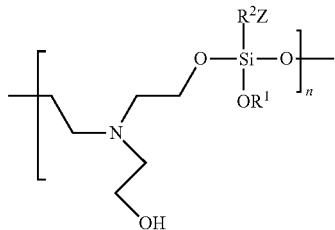

wherein n is from about 1 to about 10.

In various embodiments, an antimicrobial coating formed from an antimicrobial coating composition comprising an organosilane $(R^1O)_3Si-R^2-Z$ and triethanolamine comprises the polymeric species:

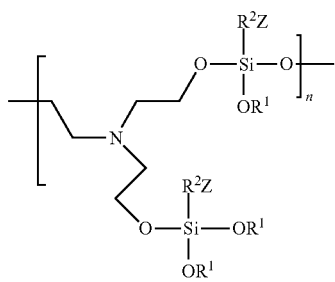

wherein n is from about 1 to about 10.

In various embodiments, an antimicrobial coating formed from an antimicrobial coating composition comprising an organosilane $(R^1O)_3Si-R^2-Z$ and triethanolamine comprises the polymeric species:

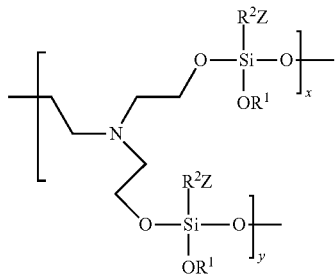

wherein x and y are independently from about 1 to about 10.

In various embodiments, a residual antimicrobial coating formed from an antimicrobial coating composition comprising an organosilane $(R^1O)_3Si-R^2-Z$ and triethanolamine comprises the polymeric species:

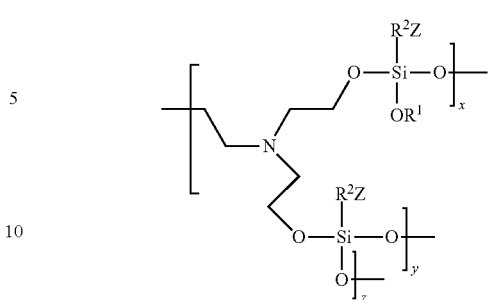

wherein x, y, and z are independently from about 1 to about 10.

In other embodiments, a residual antimicrobial coating composition comprises an orthosilicate of general structure $(R^1O)_4Si$, wherein $R^1$ is alkyl, substituted alkyl, aryl, or substituted aryl. In various embodiments the antimicrobial coating composition comprises an orthosilicate $(R^1O)_4Si$ and at least one organic amine $R^9R^{10}R^{11}N$, wherein $R^1$ is alkyl, substituted alkyl, aryl, or substituted aryl, and wherein $R^9$, $R^{10}$, and $R^{11}$ are independently H, alkyl, substituted alkyl, aryl, substituted aryl, or cyclic.

In various examples, a residual antimicrobial coating composition comprises an orthosilicate $(R^1O)_4Si$, and triethanolamine, wherein $R^1$ is alkyl, substituted alkyl, aryl, or substituted aryl. A residual antimicrobial coating formed from this antimicrobial coating composition comprises a crosslinked polymer network with a core structure:

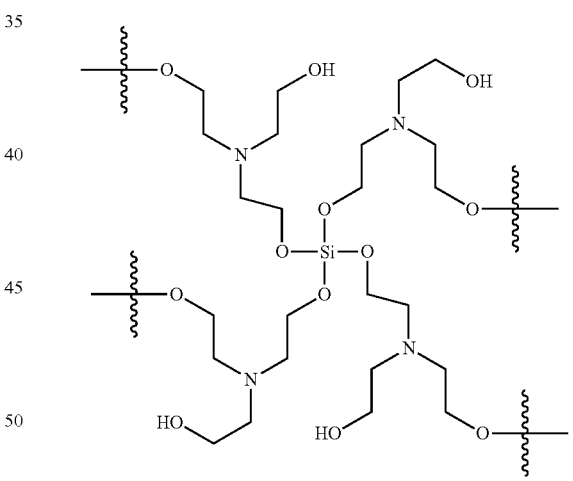

It is important to note that the polymer formed from an orthosilicate and triethanolamine comprises this structure regardless of the orthosilicate starting material, as noted from the absence of $R^1$ groups in the reaction product. The $R^1O$—substituents on silicon are exchanged with the hydroxyl substituents of the triethanolamine molecules.

In various examples, an antimicrobial coating composition comprises an orthosilicate $(R^1O)_4Si$, and diethanolamine, wherein $R^1$ is alkyl, substituted alkyl, aryl, or substituted aryl. A residual antimicrobial coating formed from this antimicrobial coating composition comprises a crosslinked polymer network with a core structure:

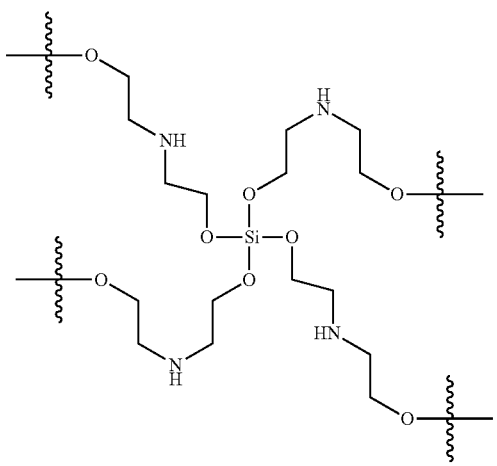 [SMILES: *OCCNCCO[Si](OCCNCCO*)(OCCNCCO*)OCCNCCO*]

It is important to note that the polymer formed from an orthosilicate and diethanolamine has this networked structure regardless of the orthosilicate starting material, as noted from the absence of $R^1$ groups in the reaction product due to the exchange of $R^1O$—substituents on silicon with the hydroxyl substituents of the diethanolamine molecules.

$TiO_2$, $Ti(OR^3)_4$, and $Ti(OR^3)_4$ Adduct Coatings

In various embodiments, a residual antimicrobial coating is formed on a medical implement or medical device by applying an antimicrobial coating composition comprising at least one Ti(IV) oxide such as $TiO_2$, a $Ti(OR^3)_4$ species, or a dimer, trimer, tetramer or polymer reaction product thereof, or a $Ti(OR^3)_4$ adduct, on the implement or the device, followed by curing including ambient or elevated temperature drying, wherein $R^3$ is alkyl, substituted alkyl, aryl or substituted aryl. As mentioned, formation of a residual antimicrobial coating may comprise this step of applying an antimicrobial coating composition comprising a Ti compound along with the application of at least one additional antimicrobial coating composition to the surface. The at least one additional antimicrobial coating composition may be applied either before or after the application of the antimicrobial coating composition comprising the Ti compound(s). In examples where more than two coatings are applied to a medical implement or device, the other antimicrobial coating compositions and the antimicrobial coating composition comprising the Ti compound(s) may be applied to the medical implement or device in any ordered sequence across any timeframe. In various embodiments, the at least one other antimicrobial coating composition comprises an organosilane.

(a) $TiO_2$ Coatings:

In various embodiments, an antimicrobial coating composition comprises $TiO_2$. The $TiO_2$ may be in any physical form, such as for example, anatase. $TiO_2$ for use in various embodiments may comprise rutile, anatase, brookite, hollandite-like, ramsdellite-like, α-PbO2-like, baddeleyite-like form, orthorhombic $TiO_2$—OI, cubic, and/or cotunnite-like forms. The most common crystalline forms are anatase, brookite and rutile. Further, an antimicrobial coating composition may comprise a $TiO_2$ sol. Any of these Ti species may be used to form a residual antimicrobial thin film of $TiO_2$ on the surfaces of a medical implement or device. To produce such a thin film on a medical implement or device, e-beam evaporation, sputtering, chemical vapor deposition, electrostatic spray, or the hydrolytic sol-gel process may be used to form a thin film $TiO_2$ coating from an antimicrobial coating composition.

In certain examples, an antimicrobial coating composition comprises a colloidal suspension of from about 0.5 wt. % to about 50 wt. % $TiO_2$ in water. In other examples, an antimicrobial coating composition comprises an aqueous mixture of Ti—$(O-i-C_3H_7)_4$ usable to create a thin film of $TiO_2$ via the sol-gel process. Such compositions may also comprise an organic solvent, such as an alcohol like n-propanol or n-butanol, a surfactant, or an acid catalyst. In the sol-gel process, $TiO_2$ is prepared by hydrolysis, condensation and polycondensation of a titanium alkoxide, such as Ti—$(O-i-C_3H_7)_4$ or $TiCl_4$. A $TiO_2$ sol-gel composition, when coated onto a medical implement or device by spray pyrolysis or other application method, provides a thin film $TiO_2$ coating on the implement or device.

In various embodiments, a residual antimicrobial coating comprises $TiO_2$. In other examples, a residual antimicrobial coating comprises $TiO_2$ formed by coating a medical dressing with a colloidal suspension of $TiO_2$ particles. In certain examples, a residual antimicrobial coating comprises $TiO_2$ synthesized by the sol-gel process, as discussed herein above for the titanyl-oxide moieties.

(b) $Ti(Or^3)_4$ Coatings:

In various embodiments, a coating composition comprises $Ti(OR^3)_4$, wherein $R^3$ is alkyl, substituted alkyl, aryl, or substituted aryl, and wherein the four separate $R^3$ groups are identical or different. Examples of $Ti(OR^3)_4$ include, but are not limited to, titanium tetramethoxide, titanium tetraethoxide, titanium methoxide triethoxide, titanium tetra-n-propoxide, titanium tetra-i-propoxide, and titanium tetraphenoxide. Depending on the physical properties of the titanium (IV) species, the compound may be used neat (e.g. Ti—(O-i-$C_3H_7)_4$) as an antimicrobial coating composition or dissolved in an alcohol or other organic solvent(s), such as the corresponding alcohol, where feasible, (methanol, ethanol, i-propanol, etc.). Thus, an antimicrobial coating composition may comprise a solution of Ti—$(O-i-C_3H_7)_4$ in isopropanol or some other alcohol.

In various embodiments, an antimicrobial coating composition comprises $Ti(OR^3)_4$, wherein $R^3$ is alkyl, substituted alkyl, aryl, or substituted aryl. In certain aspects, an antimicrobial coating composition further comprises a solvent selected from the group consisting of water, alkanols, diols, triols, chlorinated organic solvents, ethers, amines, esters, ketones, aldehydes, lactones, phenolics, and mixtures thereof. In certain examples, a solvent is selected from, but not limited to, water, methanol, ethanol, n-propanol, i-propanol, ethylene glycol, 1,2-propanediol, 1,3-propanediol, glycerin, methylene chloride, trichloromethane, carbon tetrachloride, ethylene glycol monoalkyl ether, ethylene glycol dialkylether, propylene glycol monoalkyl ether, propylene glycol dialkyl ether, ethylene glycol monophenyl ether, ethylene glycol diphenyl ether, propylene glycol monophenyl ether, propylene glycol diphenyl ether, diethylether, tetrahydrofuran, pyridine, triethanolamine, diethanolamine, triethylamine, ethylacetate, acetone, furfural, and N-methyl-2-pyrrolidone, and combinations thereof. In various examples, an antimicrobial coating composition consists essentially of Ti—$(O-i-C_3H_7)_4$. Other examples include an antimicrobial coating composition comprising Ti—$(O-i-C_3H_7)_4$ and an alcohol, and a composition comprising Ti—$(O-i-C_3H_7)_4$ and isopropanol.

In various embodiments, an antimicrobial coating composition comprising $Ti(OR^3)_4$, wherein each $R^3$ is alkyl, substituted alkyl, aryl, or substituted aryl, is applied to at least one surface of a medical implement or a medical device in order to provide a residual antimicrobial coating on the implement or device. The application method may be a spray method or a dip method of coating. The resulting wetted implement or device is then allowed to dry at ambient, or under controlled conditions (e.g. a particular % RH), or is dried under heated conditions, (e.g. a thermal convection oven or an autoclave) to produce the residual antimicrobial coating. The resulting dried coating is substantially free of all solvents. In various examples, an antimicrobial coating composition comprising Ti—(O-i-$C_3H_7)_4$ and an alcohol is applied to a medical implement or device and the alcohol is allowed to evaporate, or alternatively, the implement or device is mechanically dried, until the residual antimicrobial coating on the implement or device has no more than about 5 wt. % alcohol remaining. In various embodiments, the amount of remaining alcohol after drying is no more than about 1 wt. %. In other embodiments, the amount of remaining alcohol after drying is negligible, (e.g. less than about 0.01 wt. %). In instances wherein the $Ti(OR^3)_4$ species dimerizes, trimerizes, or polymerizes, the resulting moles of alcohol $R^3$—OH is liberated from the surface of the medical implement or device as the coating dries thereon.

In general, the bulkier the $R^3$ groups on $Ti(OR^3)_4$, the more likely the titanium species exists as a monomer, even when dried on a surface. On the other hand, $Ti(OCH_3)_4$, $Ti(OCH_3)(OCH_2CH_3)_3$, and $Ti(OCH_2CH_3)_4$, are known to exist as tetramers in the solid state. Polymerization takes place when titanium alkoxides are hydrolyzed to metal hydroxides or oxides. Thus, for example, the steric size of the $R^3$ groups can be chosen, and the humidity present during drying/curing of a coated medical implement or device can be controlled, such that monomeric, dimeric, trimeric, tetrameric or polymeric titanium species result on the surface of the medical implement or device.

In various embodiments, a residual antimicrobial coating on a medical implement or device comprises $Ti(OR^3)_4$, wherein each $R^3$ is alkyl, substituted alkyl, aryl, or substituted aryl. In other embodiments, a residual antimicrobial coating on a medical implement or device comprises the dimer:

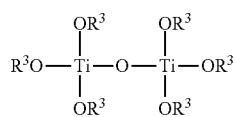

In various embodiments, a residual antimicrobial coating on a medical implement or device comprises the trimer:

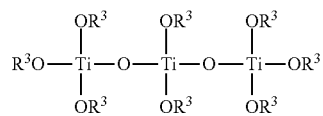

In various embodiments, a residual antimicrobial coating on a medical implement or device comprises the tetramer:

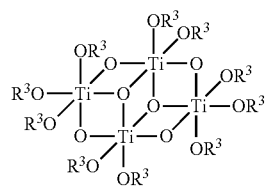

In various embodiments, a residual antimicrobial coating on a medical implement or device comprises the linear polymer:

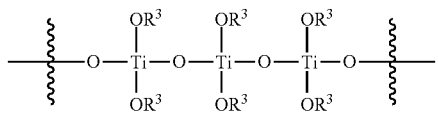

In various embodiments, a residual antimicrobial coating on a medical implement or device comprises the crosslinked polymer:

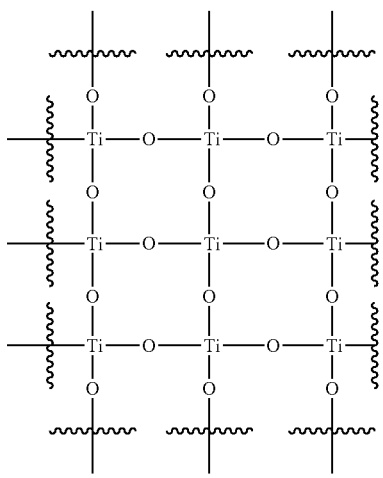

In various embodiments, a residual antimicrobial coating on a medical implement or medical device comprises the polymeric species $Ti_{3(x+1)}O_{4x}(OR^3)_{4(x+3)}$, wherein x=0, 1, 2, . . . ,∞, and wherein $R^3$ is a relatively sterically small substituent, such as methyl, ethyl, n-propyl, and i-propyl, or combinations of these $R^3$ groups.

Other aspects of titanium alkoxide chemistry is disclosed in J. H. Clark, "The Chemistry of Titanium, Zirconium and Hafnium," Pergamon Texts in Inorganic Chemistry, Volume 19, 1973, Pergamon Press, Oxford, England.

c) $Ti(OR^3)_4$ Adduct Coatings:

In various embodiments, an antimicrobial coating composition may comprise a titanium (IV) alkoxide and a diol, α-hydroxy acid, or β-hydroxy acid, and optionally any excipient such as solvent, surfactant, acid, or base. These reactants may combine to form various adducts in solution (i.e. within the composition), or may form adducts while curing or once cured onto a surface. In various examples, an antimicrobial coating composition comprises a titanium (IV) alkoxide, $Ti(OR^3)_4$ wherein each $R^3$ is alkyl, substituted alkyl, aryl, or substituted aryl, and a cis- or trans-1,2-diol, an α-hydroxy acid, or a β-hydroxy acid. When a small molecular weight alcohol is used as a solvent, the $R^3$ groups on the Ti may or may not exchange out with the alcohol. Thus the examples provided below assume there is no alcohol used, or that the alcohol does not exchange out.

A 1,2-diol for use in various embodiments may comprise ethylene glycol, 1,2-propylene glycol, 1,2-dihydroxybutane, and so forth, or any diol of general structure $R^5R^6C(OH)$—$C(OH)R^7R^8$, wherein $R^5$, $R^6$, $R^7$ and $R^8$ are independently H, alkyl, substituted alkyl, aryl, or substituted aryl. Further, and in accordance to this general structure, a 1,2-diol may comprise a dicarboxylic acid having the general structure:

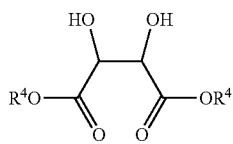

wherein $R^4$=H, alkyl, substituted alkyl, aryl, or substituted aryl. In certain examples, the 1,2-diol comprises tartaric acid or the corresponding mono- or diester.

In other examples, an α-hydroxy acid, such as glycolic acid, lactic acid, citric acid, or mandelic acid, may be used. Further, a β-hydroxy acid, such as salicylic acid, 3-hydroxypropionic acid, or carnitine may be used.

In various examples, an antimicrobial coating composition comprises at least one of $Ti(OR^3)_4$ wherein each $R^3$ is alkyl, substituted alkyl, aryl, or substituted aryl, a cis- or trans-1,2-diol of formula $R^5R^6C(OH)$—$C(OH)R^7R^8$, and an adduct of general structure:

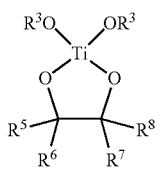

wherein $R^5$, $R^6$, $R^7$ and $R^8$ are independently H, alkyl, substituted alkyl, aryl, or substituted aryl.

In various examples, an antimicrobial coating composition comprises at least one of $Ti(OR^3)_4$ wherein each $R^3$ is alkyl, substituted alkyl, aryl, or substituted aryl, an α-hydroxy acid of formula $R^5R^6C(OH)$—$CO_2H$, and an adduct of general structure:

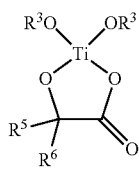

wherein $R^5$, and $R^6$ are independently H, alkyl, substituted alkyl, aryl, or substituted aryl.

In various examples, an antimicrobial coating composition comprises at least one of $Ti(OR^3)_4$ wherein each $R^3$ is alkyl, substituted alkyl, aryl, or substituted aryl, a β-hydroxy acid of formula $R^5R^6C(OH)$—$C(R^7)(R^8)CO_2H$, and an adduct of general structure:

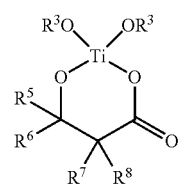

wherein $R^5$, $R^6$, $R^7$ and $R^8$ are independently H, alkyl, substituted alkyl, aryl, or substituted aryl.

In various embodiments, an antimicrobial composition comprising $Ti(OR^3)_4$ wherein each $R^3$ is alkyl, substituted alkyl, aryl, or substituted aryl, and a cis- or trans-1,2-diol, an α-hydroxy acid, or a β-hydroxy acid is applied to a medical implement or a medical device to provide a residual antimicrobial coating on the implement or device. These compositions may be applied for use in various embodiments, such as by spray coating or dip coating. The coated implement or device may then be cured, such as by ambient drying, annealing or autoclave.

In various embodiments, a residual antimicrobial coating comprises a titanium adduct of general structure:

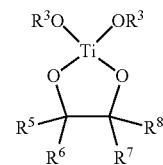

wherein $R^3$ is alkyl, substituted alkyl, aryl, or substituted aryl and $R^5$, $R^6$, $R^7$ and $R^8$ are independently H, alkyl, substituted alkyl, aryl, or substituted aryl.

In various embodiments, a residual antimicrobial coating comprises a titanium adduct of general structure:

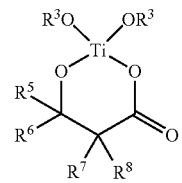

wherein $R^3$ is alkyl, substituted alkyl, aryl, or substituted aryl and $R^5$, $R^6$, $R^7$ and $R^8$ are independently H, alkyl, substituted alkyl, aryl, or substituted aryl.

In various embodiments, a residual antimicrobial coating comprises a titanium adduct of general structure:

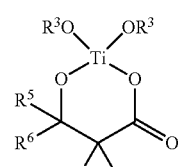

wherein $R^3$ is alkyl, substituted alkyl, aryl, or substituted aryl and $R^5$, $R^6$, $R^7$ and $R^8$ are independently H, alkyl, substituted alkyl, aryl, or substituted aryl.

Coatings comprising an organosilane, amine, and a titanium species, or reaction products therefrom, and organosilane and amine coatings in combination with a coating comprising a titanium species (a) Antimicrobial Coating Compositions Comprising an Organosilane, an Amine and a Titanium Species:

In various embodiments, an antimicrobial coating composition comprises a mixture of an organosilane structure $(R^1O)_3Si$—$R^2$—Z, an amine $R^9R^{10}R^{11}N$, and a titanium species $Ti(OR^3)_4$, wherein each $R^1$ is independently H, alkyl, substituted alkyl, aryl, or substituted aryl, $R^2$ is a bivalent linker, each $R^3$ is independently alkyl, substituted alkyl, aryl, or substituted aryl, and $R^9$, $R^{10}$, and $R^{11}$ are independently H, alkyl, substituted alkyl, aryl, substituted aryl, or cyclic. In various examples, a titanium (IV) species comprises the species, $Ti(OR^3)_{3O}-(CH_2)_q-R^{12}$, wherein $R^{12}$ comprises a chromophore and q is from about 1 to about 10. Chromophore $R^{12}$ may comprise any chromophore that upon exposure to electromagnetic irradiation having a first frequency emits electromagnetic radiation of a second frequency different from the first. In certain embodiments, the first frequency is within the UV spectrum and the second frequency is within the visible spectrum. In certain embodiments, $R^{12}$ comprises a triscyclometalated iridium (III) material that, upon exposure to UV irradiation, emits visible light. A titanium species such as $Ti(OR^3)_4$ or $Ti(OR^3)_{3O}-(CH_2)_q-R^{12}$ may be copolymerized with an organosilane.

When a medical implement or medical device is treated with such a composition and the coating cured thereon, the resulting residual antimicrobial coating formed on the medical implement or device may comprise any combination of unreacted organosilane, amine and titanium species along with various hydrolysis products, self-condensation products including homopolymers, intermolecular adducts, and intermolecular polymeric reaction products of various linear, branched and dendritic structure.

In various embodiments, a residual antimicrobial coating comprises a polymer having the structure:

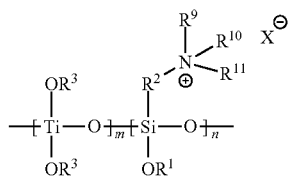

wherein m and n are independently from 1 to about 500.

In various embodiments, an antimicrobial coating composition comprises an organosilane $(R^1O)_3Si-R^2-Z$, an amine $R^9R^{10}R^{11}N$, and a titanium species $Ti(OR^3)_3O-(CH_2)_q-R^{12}$, wherein each $R^1$ is independently H, alkyl, substituted alkyl, aryl, or substituted aryl, $R^2$ is a bivalent linker, each $R^3$ is independently alkyl, substituted alkyl, aryl, or substituted aryl, $R^9$, $R^{10}$, and $R^{11}$ are independently H, alkyl, substituted alkyl, aryl, substituted aryl, or cyclic, $R^{12}$ is a chromophore, and q is from about 1 to about 10.

When this antimicrobial coating composition is cast onto a medical implement or medical device and cured thereon, the resulting residual antimicrobial coating comprises a polymer having structure:

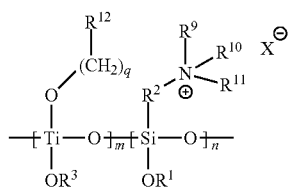

wherein m and n are independently from 1 to about 500. These polymers may comprise linear or crosslinked structures. In more specific examples, $R^2$ is $-CH_2-$, $-CH_2CH_2-$, $-CH_2CH_2CH_2-$, or $-CH_2CH_2-O-CH_2(CH_2CH_2)p-$, wherein p is from 0 to about 5.

(b) Residual Antimicrobial Coatings Comprising an Organosilane and Amine Coating in Combination with a Coating Comprising a Titanium Species:

In certain aspects, a residual antimicrobial coating formed from an antimicrobial coating composition comprising an organosilane $(R^1O)_3Si-R^2-Z$ and an amine $R^9R^{10}R^{11}N$, may further comprise a coating obtained by casting an antimicrobial coating composition comprising any titanium species including any form of $TiO_2$, any Ti (IV) oxide $Ti(OR^3)_4$ or compounds such as $Ti(OR^3)_3O-(CH_2)_q-R^{12}$. The coating comprising the at least one titanium species may be disposed underneath or overtop of an organosilane/amine coating. For example, an organosilane/amine layer may be disposed between the surface of the medical implement or device and the Ti species layer. There may be any number of organosilane/amine coatings and titanium species coatings, disposed in any order of the layers. Further, any degree of curing may be used for any of the coatings, and each of the coatings may be spaced apart by any time period, such as seconds, minutes, hours, days, months, etc. When medical implements and devices begin to lose their residual antimicrobial efficacy, they may be recoated by any combination of organosilane/amine and titanium species coatings.

In various embodiments, a method of forming a residual antimicrobial coating on the surface of a medical implement or medical device, including portions of surfaces of implantable devices and components of medical instruments, comprises: (1) disposing on a portion of a surface of the device or implement an aqueous antimicrobial coating composition comprising at least one organosilane $(R^1O)_3Si-R^2-Z$, wherein $R^1$ is H, alkyl, substituted alkyl, aryl, or substituted aryl, $R^2$ is a bivalent linker, and Z is a nucleophile, a leaving group or a quaternary ammonium group; and (2) disposing on the portion of the surface an aqueous solution of a titanyl sol. In various examples, steps (1) and (2) can be performed in either order or simultaneously. In various embodiments, the organosilane comprises at least one of 3-(trimethoxysilyl)-propyldimethyloctadecyl ammonium chloride, 3-(trihydroxysilyl)-propyldimethyloctadecyl ammonium chloride, 3-chloropropyltrimethoxysilane, 3-chloropropyltriethoxysilane, 3-chloropropylsilanetriol, 3-aminopropyltrimethoxysilane, 3-aminopropyltriethoxysilane, and 3-aminopropylsilanetriol. In various embodiments, the aqueous antimicrobial coating composition further comprises at least one amine such as diethanolamine or triethanolamine. In various examples, the aqueous antimicrobial coating composition comprises a mixture of 3-(trihydroxysilyl)-propyldimethyloctadecyl ammonium chloride, 3-chloropropyltrimethoxysilane, and triethanolamine. In various examples, the titanyl sol comprises any titanium species capable of forming a $TiO_2$ thin film. In various examples, the aqueous titanyl sol comprises an 0.85 wt. % mixture of peroxotitanium acid and peroxo-modified anatase sol.

As discussed, when various antimicrobial coating compositions dry and/or are cured by other methods on a surface of an implement or device, reactions may take place between the organosilane and the amine, between the amine and the titanium species, between the organosilane and the titanium species, or between all three.

Organosilane Coating, Overcoated or Undercoated with a Titanium Species

In certain aspects, a residual antimicrobial coating formed from an antimicrobial coating composition comprising an organosilane $(R^1O)_3Si-R^2-Z$ may further comprise a coating obtained by casting an antimicrobial coating composition comprising any titanium species including any form of $TiO_2$, any Ti (IV) oxide $Ti(OR^3)_4$ or compounds such as $Ti(OR^3)_3O—(CH_2)_q—R^{12}$. The coating comprising the at least one titanium species may be disposed underneath or overtop of an organosilane coating. There may be any number of organosilane coatings and titanium species coatings, disposed in any order of the layers. Further, any degree of curing may be used for any of the coatings, and each of the coatings may be spaced apart by any time period, such as seconds, minutes, hours, days, months, etc. When medical implements and devices begin to lose their residual antimicrobial efficacy, they may be recoated by any combination of organosilane and titanium species coatings.

As discussed, when various antimicrobial coating compositions dry and/or are cured by other methods on a surface, reactions may take place between the organosilane and the titanium species.

Grafted Parylene Polymer Coatings

Palladium catalyzed amination of parylene C:

In various embodiments, an antimicrobial coating composition comprises the reaction product between parylene C and at least one organosilane $(R^1O)_3Si—R^2—Z$, wherein each $R^1$ is independently H, alkyl, substituted alkyl, aryl, or substituted aryl, $R^2$ is a bivalent linker and Z is $—NH_2$. The grafted polymer may be produced by the Buchwald-Hartwig cross-coupling reaction, whereby the organosilane $(R^1O)_3Si—R^2—Z$ is reacted with parylene C in the presence of a palladium catalyst such as $PdCl_2$ (dppf). The polymer thus obtained comprises the structure:

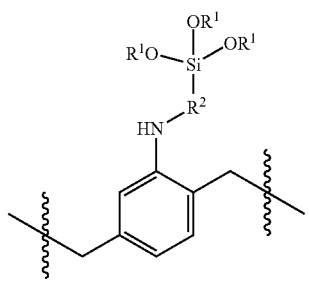

An antimicrobial coating composition comprising this polymer may be applied to a medical implement or device by any of the methods for use in various embodiments, including vapor phase deposition.

In various embodiments of the present disclosure, a coating composition comprises a polymer:

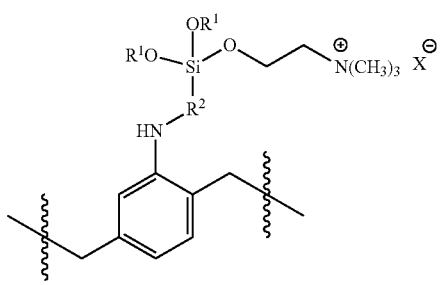

wherein $R^1$ is independently H, alkyl, substituted alkyl, aryl, or substituted aryl, $R^2$ is a bivalent linker, and X is chloride or bitartrate. This parylene polymer may be produced by reaction of the grafted polymer with a choline salt such as choline chloride or choline bartartrate. An antimicrobial coating composition comprising this polymer may be applied to a medical implement or device by any of the methods described herein, including vapor phase deposition.

Other Grafted Parylene Polymers:

Other grafted polymers based on the parylene structure may be envisioned. Such grafted polymers may comprise parylene C, parylene D or any other parylene as the starting material and an organosilane of general structure $(R^1O)_3Si—R^2—Z$, wherein each $R^1$ is independently H, alkyl, substituted alkyl, aryl, or substituted aryl, $R^2$ is a bivalent linker and Z is a nucleophile or leaving group.

GENERAL METHODS AND EMBODIMENTS

Urinary Catheter—Silicon Rubber

To simulate the residual antimicrobial efficacy on a urinary catheter, such as a Foley catheter, a test coupon made of a common catheter material can be used as a surrogate. The most common catheter materials are silicones, such as polydimethylsiloxane, polyvinyl chloride (PVC) and latex rubber. Latex has been used since the 1930's for urinary catheters, but continues to present allergy issues.

1/16" or 1/8" thick silicon rubber test coupons, available from Metex Corporation Ltd., Toronto, Canada, would be immersed in or spray coated with an antimicrobial coating composition comprising (i) at least one organosilane $(R^1O)_3Si—R^2—Z$; and (ii) at least one amine $R^9R^{10}R^{11}N$, wherein $R^1$ is H, alkyl, substituted alkyl, aryl or substituted aryl, $R^2$ is a bivalent linker, Z is a nucleophile, leaving group, or quaternary nitrogen substituent, and $R^9$, $R^{10}$, and $R^{11}$ are independently H, alkyl, substituted alkyl, aryl, substituted aryl or cyclic.

The wetted coupons would then be allowed to dry in ambient conditions and then optionally thermally treated. To simulate frequent handling of a Foley catheter, the treated silicone rubber substrates may be wear testing by wedging the test coupon into a Gardner Straight-Line Abrasion Tester (from Qualitest USA, Ft. Lauderdale, FL), abrading the surface with a dry cloth placed in the weighted carriage, and inoculating the worn surface in accordance with EPA Protocol #01-1A, entitled "Protocol for Residual Self-Sanitizing Activity of Dried Chemical Residues on Hard, Non-Porous Surfaces. The test organism may be, for example, E. coli. Inoculations at wear=0 (control) and at wear times simulating several hours of frequent handling and use, as compared to the negative control coupons not having any coating, would demonstrate residual antimicrobial efficacy on silicon rubber, which is relatable to the performance expected on a silicon rubber urinary catheter, such as a Foley catheter.

Medical Device Coating with Reactive Silane and Amine—in General

The surfaces of a medical implement or medical device can be immersion coated or sprayed with an antimicrobial coating composition comprising (i) at least one organosilane $(R^1O)_3Si—R^2—Z$; and (ii) at least one amine $R^9R^{10}R^{11}N$, wherein $R^1$ is H, alkyl, substituted alkyl, aryl or substituted aryl, $R^2$ is a bivalent linker, Z is a nucleophile, leaving group, or quaternary nitrogen substituent, and $R^9$, $R^{10}$, and $R^{11}$ are independently H, alkyl, substituted alkyl, aryl, substituted aryl or cyclic. After about 15 minutes, the implement or device can be optionally sprayed with an antimicrobial coating composition comprising at least one titanium species, including any form of $TiO_2$, a sol-gel to provide a $TiO_2$ thin film, any Ti (IV) oxide, $Ti(OR^3)_4$ or compounds such as $Ti(OR^3)_{30}—(CH_2)_q—R^{12}$.

In variations of this example, the order of the two applications may be reversed such that the Ti-containing composition is applied first to the implement or device.

Medical Device Coating with Titanium-Tartaric Acid Adduct 9.0 grams of tartaric acid are dissolved in 0.120 liters of water in an Erlenmeyer flask to give a 0.5 molar solution. This solution is stirred overnight at room temperature. The following day, the tartaric acid solution is filtered to remove particulates. 25 mL of filtered 0.5 M tartaric acid (0.01249 moles of tartaric acid) is poured into a round bottom flask and chilled on ice with stirring. 3.69 grams of titanium (IV) isopropoxide is added in 1 mL aliquots until all of it is added to the tartaric acid solution.

Upon addition of the titanium (IV) isopropoxide the ice bath is removed. The mixture remains a solution for approximately 10 minutes after which it becomes an opaque (white) gel. The gel is stirred at RT overnight. The gelatinous material is mixed with water, or alcohol and water. This resulting antimicrobial coating composition may be applied by any of the methods disclosed herein onto a medical implement or medical device.

In various embodiments, the molar ratio of the tartaric acid/Ti(IV) oxide may be varied, and/or the tartaric acid may be substituted by another 1,2-diol, an α-hydroxy acid, or a 3-hydroxy acid. In other variations of this example, any titanium (IV) alkoxide may be used.

In various embodiments, coating a medical device with the titanium(IV)/tartaric acid adduct may be preceded by, or followed by, a coating of at least one organosilane as described herein.

Medical Device Coating with Quaternary Silane and Titanium Species

The surfaces of a medical implement or medical device may be immersed in or sprayed with an aqueous solution of octadecylaminodimethyltrihydroxysilylpropyl ammonium chloride. Thereafter, the implement or device may be immersed in or sprayed with an antimicrobial coating composition comprising at least one of the Ti species disclosed herein, including any form of $TiO_2$, any sol-gel to form a $TiO_2$ thin film, any Ti (IV) oxide, $Ti(OR^3)_4$ or compounds such as $Ti(OR^3)_{3O}$—$(CH_2)_q$—$R^{12}$.

Medical Device Coating with Reactive Silane and Amine—Another Embodiment

The surfaces of a medical implement or medical device may be immersed in or sprayed with an antimicrobial coating composition comprising 3-aminopropyltriethoxysilane and triethanolamine. Afterwards, the implement or device may be optionally immersed in or sprayed with an antimicrobial coating composition comprising at least one titanium species, including any form of $TiO_2$, any sol-gel to form a $TiO_2$ thin film, any Ti (IV) oxide, $Ti(OR^3)_4$ or compounds such as $Ti(OR^3)_3O$—$(CH_2)_q$—$R^{12}$. The order of the two treatments may be reversed.

Nitinol Stent

A Nitinol stent can be dipped into an antimicrobial coating composition comprising at least one of an organosilane $(R^1O)_3Si$—$R^2$—$Z$, an organic amine $R^9R^{10}R^{11}N$, a titanium (IV) species, a 1,2-diol, an α-hydroxy acid, a β-hydroxy acid, and an organosilane grafted parylene polymer, wherein $R^1$ is H, alkyl, substituted alkyl, aryl or substituted aryl, $R^2$ is a bivalent linker, and Z is a nucleophile, leaving group, or quaternary nitrogen substituent, and $R^9$, $R^{10}$, and $R^{11}$ are independently H, alkyl, substituted aryl or cyclic; and a solvent comprising water and/or an alkanol. The wetted Nitinol stent can then air dried or dried in a convection oven. The stent may then be optionally coated by dip or spray methods with a second antimicrobial composition comprising at least one Ti(IV) oxide in water and/or alkanol. The Nitinol stent thus coated may then be thermally cured or cured by radiation, and sterilized by any method prior to being packaged in sterile packaging.

In various embodiments, a Nitinol test coupon can be used as a test surrogate for an actual stent. For this purpose, Nitinol sheet coupons, item number #83141, measuring 1.968"× 1.968" and 0.0149" thick, available from Johnson Matthey, Inc., West Chester, PA, may be coated with an antimicrobial coating composition comprising at least one of an organosilane $(R^1O)_3Si$—$R^2$—$Z$, an organic amine $R^9R^{10}R^{11}N$, a titanium (IV) species, a 1,2-diol, an α-hydroxy acid, a β-hydroxy acid, and an organosilane grafted parylene polymer, wherein $R^1$ is H, alkyl, substituted alkyl, aryl or substituted aryl, $R^2$ is a bivalent linker, and Z is a nucleophile, leaving group, or quaternary nitrogen substituent, and $R^9$, $R^{10}$, and $R^{11}$ are independently H, alkyl, substituted alkyl, aryl, substituted aryl or cyclic; and a solvent comprising water and/or an alkanol.

In other variations, Nitinol sheet coupons, item number #83141, measuring 1.968"×1.968" and 0.0149" thick, available from Johnson Matthey, Inc., West Chester, PA, may be coated with an antimicrobial coating composition comprising at least one organosilane and at least one amine. In various embodiments, the at least one organosilane consists essentially of a mixture of octadecyldimethyl-(3-trimethoxysilylpropyl) ammonium chloride and 3-chloropropyltrimethoxysilane, and the at least one amine is triethanolamine. In various embodiments, the at least one organosilane consists essentially of 3-aminopropyltriethoxysilane, and the at least one amine is triethanolamine.

In various embodiments, the treatment of a stent with one or more antimicrobial coating compositions as disclosed herein presents a method of modifying the fluid dynamics of the stent. When a stent is placed into a vessel, such as an artery, the stent acts as an obstruction to blood flow, having a tendency to create certain eddies and other turbulence. Although stents may be structurally designed to mitigate this issue, the coatings presented herein have the potential to change the hydrophilicity/hydrophobicity of the material the stent is made from. In various embodiments, the coatings herein increase hydrophilicity of a stent surface such that blood flows more smoothly over the surfaces of the stent. In some examples, an organosilane coating on a stent increases hydrophobicity of stent surfaces, which may be desired in some instances. In other examples, a titanium(IV) species coating, either directly on the stent surfaces or over top of an organosilane coating, increases hydrophilicity, or in other words, mitigates the hydrophobicity effects of the organosilane. In various embodiments, a useful titanium(IV) species is a titanium sol-gel mixture, such as a mixture of peroxotitanium acid and peroxo-modified anatase sol.

CPAP Component Coating

In various embodiments, a method of forming a residual antimicrobial coating on a portion of a surface of a component to a CPAP or bi-PAP machine comprises: (1) disposing on a portion of a surface of the component an aqueous antimicrobial coating composition comprising at least one organosilane $(R^1O)_3Si$—$R^2$—$Z$, wherein $R^1$ is H, alkyl, substituted alkyl, aryl, or substituted aryl, $R^2$ is a bivalent linker, and Z is a nucleophile, a leaving group or a quaternary ammonium group. In various embodiments, the organosilane comprises at least one of 3-(trimethoxysilyl)-propyldimethyloctadecyl ammonium chloride, 3-(trihydroxysilyl)-propyldimethyloctadecyl ammonium chloride, 3-chloropropyltrimethoxysilane, 3-chloropropyltriethoxysilane, 3-chloropropylsilanetriol, 3-aminopropyltrimethoxysilane, 3-aminopropyltriethoxysilane, and 3-aminopropylsilanetriol. In various embodiments, the aqueous antimicrobial coating composition further comprises at least one amine such as diethanolamine or triethanolamine. In various embodiments, the at least one organosilane consists essentially of a mixture of octadecyldimethyl-(3-trimethoxysilylpropyl) ammonium chloride and 3-chloropropyltrimethoxysilane, and the at least one amine is triethanolamine. In various embodiments, the at least one organosilane consists essentially of 3-aminopropyltriethoxysilane, and the at least one amine is triethanolamine.

The various components of a CPAP machine that may be coated with a residual antimicrobial coating include, but are not limited to, masks, mask parts, filters, hoses, machine parts and humidifier parts. Masks include, but are not limited to, nasal masks, full face masks, nasal pillow masks, nasal prong masks, hybrid masks, oral masks, and total face masks. Filters include, but are not limited to, reusable foam filters, disposable filters, bacteria filters, and filter covers. CPAP machine bacteria filters are porous filters that trap bacteria by size exclusion. The antimicrobial coatings herein provide an extra mode of action to a size exclusion bacteria filter by killing organisms trapped in the porous structure. Hoses include standard/performance, sensor lines, hoses with heating coils, short tubes and tubing, and all the various couplers and connectors for hoses. Mask parts include, but are not limited to, mask kits, cushions, pillows, headgear, headgear clips, and chinstraps. Humidifier parts include, but are not limited to, water chambers, and lids and seals for same.

These and other CPAP components may be coated by the antimicrobial coating compositions of the present disclosure by any of the methods described. For example, many of the plastic components for CPAP, such as hoses, masks, connectors, and such, may be dip coated or spray coated. In various examples, extended spray wands may be used to coat the inside of a CPAP hose.

In a non-limiting example, a CPAP hose is coated on the inside with an antimicrobial coating composition in a two-step process. The hose is a Respironics® Pure White 6-foot performance CPAP/BiPAP 19 mm diameter tubing with 22 mm ends. The rubber ends comprise thermoplastic elastomer. The walls of the hose comprise metallocene polyethylene and the helix of the hose comprises polypropylene. The hose is treated by circulated an aqueous antimicrobial coating composition through the hose for several minutes, the composition comprising a mixture of at least one organosilane and at least one amine. In various embodiments, the at least one organosilane consists essentially of a mixture of octadecyldimethyl-(3-trimethoxysilylpropyl) ammonium chloride and 3-chloropropyltrimethoxysilane, and the at least one amine is triethanolamine. In various embodiments, the at least one organosilane consists essentially of 3-aminopropyltriethoxysilane, and the at least one amine is triethanolamine.

Drying at ambient or with forced warm air provides a residual antimicrobial coating inside the hose. Air passing through the hose is sanitized by contact of organisms with the inside wall of the hose. In variations of this method, the inside of the hose may be further treated with an aqueous mixture of 0.85 wt. % peroxotitanium acid and peroxo-modified anatase sol by flowing the aqueous titanium sol through the hose to coat the inside length of the hose.

In a variation of the method, the hose is treated by circulated an aqueous antimicrobial coating composition through the hose for several minutes, the composition comprising a mixture of at least one organosilane and at least one amine. Optionally, an aqueous mixture of 0.85 wt. % peroxotitanium acid and peroxo-modified anatase sol may be flowed through to coat the inside length of the hose. Drying at ambient or with forced warm air provides a residual antimicrobial coating inside the hose. Air passing through the hose is sanitized by contact of organisms with the inside wall of the hose.

Examples

Formulations

In the following examples, two separate coating compositions were prepared and given the internal designations 2030 and 2015, as follows:

2030 was prepared by combining 10% v/v 3-aminopropyltriethoxysilane (herein "3-APTES" or more simply, "APTES") and 0.28% v/v triethanolamine (herein "TEA"), with the remainder being water.

2015 was prepared by combining 0.75 wt. % octadecyldimethyl-(3-trimethoxysilylpropyl) ammonium chloride (herein "DMOD"), 0.12 wt. % 3-chloropropyltrimethoxysilane (herein "CPTMS"), and 0.045 wt. % TEA, with the remainder being water.

Example 1: Metal and Silicone Rubber Coating—Providing Antimicrobial Surfaces on Metal Surfaced Devices, Silicone Rubber Foley Catheter and CPAP Components, and Stainless Steel Medical Implements Substrates In the examples, three representative 1 inch×1 inch test coupons were used: Nitinol, which is representative of the material used in many medical implants, such as stents; Silicone rubber, which is representative of the material used in both Foley catheters and CPAP/bi-PAP parts; and stainless steel (316 grade), which is representative of the material used in many medical implements. In certain examples, coupons were allowed to dry at ambient and then subjected to thermal treatment on a hot plate. In other examples, the 316 stainless coupons were first allowed to dry at ambient and then autoclaved at 121° C. for 20 minutes after treatment with an antimicrobial coating. Immersion followed by autoclaving was meant to exemplify a hygienic procedure that would be used to prep medical implements in a hospital.

General Procedures

The following laboratory methods are designed to mimic industrial processes and hospital procedures.

Coating Procedure:

1. Each test carrier coupon was placed in a separate sterile petri dish.

2. 1 mL of either the 2030 or 2015 formulation was pipetted on the carrier to simulate immersion coating.

3. Each wetted carrier was then left in its petri dish to air dry under ambient conditions.

4. The air dried carriers were then either placed on a hot plate for 1 hour at 100° C. to simulate the curing of the coating on a medical device, or were autoclaved for 20 minutes at 121° C. to simulate treatment of medical implements in a hospital by medical care workers. The data tables indicate if carriers were autoclaved. If a substrate is indicated as not having been autoclaved, then it means the substrate coupon was air dried at ambient and then heated on the hot plate.

Sanitizer Test

1. A frozen aliquot of S. epidermidis ATCC 12228 (or E. aerogenes ATCC 13048) was thawed, a loop of same was streaked on a TSA or Nutrient agar plate, and the plate incubated for 48 hours at 37° C.
2. One colony from each plate was inoculated in 20 ml of respective broth and incubated for 24 hours at 37° C.
3. The culture was diluted 1:10 in deionized $H_2O$ with 5% fetal bovine serum (108 CFU/ml).
4. Carriers were inoculated with 0.010 ml of test culture (about $1 \times 10^6$ CFU/carrier) onto the center and spread over the surface area using a sterile bent pipette tip, with care not to spread on to the edges.
5. One set of uncoated control carriers was harvested immediately (zero hour) by immersing in 25 ml of letheen broth, vortexed for 1 min, serially diluted $10^{-2}$ to $10^{-4}$ in PBS buffer, and pour-plated with cooling TSA.
6. The carriers were placed in an incubator at 30° C. at 50% humidity. At completion of contact times (1 and 2 h for 2030-coated carriers, 2 and 4 h for 2015-coated carriers), the carriers were neutralized as per Step 5. Uncoated and control carriers were pour-plated at $10^{-2}$ to $10^{-3}$, and coated carriers were pour-plated at 100 to 10-2.
7. The plates were inverted and incubated at 37° C. for 48 hours, and then scored by directly counting the colonies.
8. $Log_{10}$ and percent reductions were calculated relative to the timed controls.

Results

TABLE 1 shows the residual antimicrobial efficacy results obtained for various medical device and medical implement materials previously coated with the 2030 composition and tested against S. epidermidis ATCC 12228. As indicated in the table, one group of the stainless steel coupons was wetted with the 2030 composition, air dried at ambient, and then autoclaved at 121° C. for 20 minutes to emulate a procedure for preparing medical implements in a hospital. In the table, the asterisk (*) indicates the groups that reached the limit of detection. Log and percent reduction are compared to time control group (uncoated carriers). Replicates: N=2 carriers per uncoated control and coated groups. Detection limit was 1 bacterium in 25 mL neutralizer broth=25 CFU/carrier.

TABLE 1

Results for 2030 coated carriers challenged with S. epidermidis ATCC 12228
2030-Coated Medical Devices Test-S. epidermidis ATCC 12228

| Material | Coating | Contact Time (hr.) | Geo. mean (CFU/carrier) | Log10 Reduction | Percent Reduction |
|---|---|---|---|---|---|
| Nitinol | None | 0 | 9.96E+05 | N/A | |
| Silicone Rubber | | | 1.15E+06 | N/A | |
| Stainless Steel | | | 9.85E+05 | N/A | |
| Nitinol | None | 1 | 6.08E+05 | N/A | |
| | 2030 | | 1.26E+03 | 2.68 | 99.79% |
| | None | 2 | 2.33E+05 | N/A | |
| | 2030 | | 4.68E+02 | 2.70 | 99.80% |
| Silicone Rubber | None | 1 | 1.22E+06 | N/A | |
| | 2030 | | 1.90E+02 | 3.81 | 99.98% |
| | None | 2 | 1.05E+06 | N/A | |
| | 2030 | | 1.93E+03 | 2.74 | 99.82% |
| Stainless Steel | None | 1 | 5.31E+05 | N/A | |
| | 2030 | | 4.44E+03 | 2.08 | 99.16% |
| | 2030 | | 2.50E+01 | 4.33 | 99.995%* |
| | (autoclaved) | | | | |

TABLE 1-continued

Results for 2030 coated carriers challenged with S. epidermidis ATCC 12228
2030-Coated Medical Devices Test-S. epidermidis ATCC 12228

| Material | Coating | Contact Time (hr.) | Geo. mean (CFU/carrier) | Log10 Reduction | Percent Reduction |
|---|---|---|---|---|---|
| | None | 2 | 1.57E+05 | N/A | |
| | 2030 | | 4.09E+03 | 1.58 | 97.39% |
| | 2030 (autoclaved) | | 1.85E+02 | 2.93 | 99.88% |

TABLE 2 shows the residual antimicrobial efficacy results obtained for various medical device and medical implement materials previously coated with the 2015 composition and tested against S. epidermidis ATCC 12228. As indicated in the table, one group of the stainless steel coupons was wetted with the 2015 composition, air dried at ambient, and then autoclaved at 121' C for 20 minutes to emulate a procedure for preparing medical implements in a hospital. In the table, the asterisk (*) indicates the groups that reached the limit of detection. Log and percent reduction are compared to time control group (uncoated carriers). Replicates: N=2 carriers per uncoated control and coated groups. Detection limit was 1 bacterium in 25 mL neutralizer broth=25 CFU/carrier.

TABLE 2

Results for 2015 coated carriers challenged with S. epidermidis ATCC 12228
2015-Coated Medical Devices Test-S. epidermidis ATCC 12228

| Material | Coating | Contact Time | Geo. mean (CFU/carrier) | Log10 Reduction | Percent Reduction |
|---|---|---|---|---|---|
| Nitinol | None | 0 | 9.96E+05 | N/A | |
| Silicone Rubber | | | 1.15E+06 | N/A | |
| Stainless Steel | | | 9.85E+05 | N/A | |
| Nitinol | None | 2 | 2.33E+05 | N/A | |
| | 2015 | | 3.75E+01 | 3.79 | 99.98% |
| | None | 4 | 9.06E+04 | N/A | |
| | 2015 | | 2.50E+01 | 3.56 | 99.97%* |
| Silicone Rubber | None | 2 | 1.05E+06 | N/A | |
| | 2015 | | 1.02E+04 | 2.01 | 99.03% |
| | None | 4 | 1.70E+05 | N/A | |
| | 2015 | | 5.23E+03 | 1.51 | 96.92% |
| Stainless Steel | None | 2 | 1.57E+05 | N/A | |
| | 2015 | | 3.54E+01 | 3.65 | 99.98% |
| | 2015 (autoclaved) | | 1.15E+02 | 3.14 | 99.93% |
| | None | 4 | 8.20E+05 | N/A | |
| | 2015 | | 2.50E+01 | 4.52 | 99.997%* |
| | 2015 (autoclaved) | | 4.33E+01 | 4.28 | 99.99% |

TABLE 3 shows the residual antimicrobial efficacy results obtained for various medical device and medical implement materials previously coated with the 2030 composition and tested against E. aerogenes ATCC 13048. As indicated in the table, one group of the stainless steel coupons was wetted with the 2030 composition, air dried at ambient, and then autoclaved at 121' C for 20 minutes to emulate a procedure for preparing medical implements in a hospital. In the table, the asterisk (*) indicates the groups that reached the limit of detection. Log and percent reduction are compared to time control group (uncoated carriers). Replicates: N=2 carriers per uncoated control and coated groups. Detection limit was 1 bacterium in 25 mL neutralizer broth=25 CFU/carrier.

TABLE 3

Results for 2030 coated carriers challenged with *E. aerogenes* ATCC 13048.
2030-Coated Medical Devices Test-*E. aerogenes* ATCC 13048

| Material | Coating | Contact Time | Geo. mean (CFU/carrier) | Log10 Reduction | Percent Reduction |
|---|---|---|---|---|---|
| Nitinol | None | 0 | 4.07E+06 | | N/A |
| Silicone Rubber | | | 4.15E+06 | | N/A |
| Stainless Steel | | | 4.77E+06 | | N/A |
| Nitinol | None | 1 | 3.41E+06 | | N/A |
| | 2030 | | 2.50E+01 | 5.13 | 99.999%* |
| | None | 2 | 8.79E+05 | | N/A |
| | 2030 | | 2.50E+01 | 4.55 | 99.997%* |
| Silicone Rubber | None | 1 | 2.24E+06 | | N/A |
| | 2030 | | 1.19E+03 | 3.27 | 99.95% |
| | None | 2 | 2.18E+06 | | N/A |
| | 2030 | | 1.82E+04 | 2.08 | 99.16% |
| Stainless Steel | None | 1 | 1.43E+06 | | N/A |
| | 2030 | | 1.73E+04 | 1.92 | 98.79% |
| | 2030 (autoclaved) | | 3.61E+02 | 3.60 | 99.97% |
| | None | 2 | 7.05E+05 | | N/A |
| | 2030 | | 1.49E+04 | 1.68 | 97.89% |
| | 2030 (autoclaved) | | 9.68E+01 | 3.86 | 99.99% |

TABLE 4 shows the residual antimicrobial efficacy results obtained for various medical device and medical implement materials previously coated with the 2015 composition and tested against *E. aerogenes* ATCC 13048. As indicated in the table, one group of the stainless steel coupons was wetted with the 2015 composition, air dried at ambient, and then autoclaved at 121° C. for 20 minutes to emulate a procedure for preparing medical implements in a hospital. Log and percent reduction are compared to time control group (uncoated carriers). Replicates: N=2 carriers per uncoated control and coated groups. Detection limit was 1 bacterium in 25 mL neutralizer broth=25 CFU/carrier.

TABLE 4

Results for 2015 coated carriers challenged with *E. aerogenes* ATCC 13048.
2015-Coated Medical Devices Test-*E. aerogenes* ATCC 13048

| Material | Coating | Contact Time | Geo. mean (CFU/carrier) | Log10 Reduction | Percent Reduction |
|---|---|---|---|---|---|
| Nitinol | None | 0 | 4.07E+06 | | N/A |
| Silicone Rubber | | | 4.15E+06 | | N/A |
| Stainless Steel | | | 4.77E+06 | | N/A |
| Nitinol | None | 2 | 8.79E+05 | | N/A |
| | 2015 | | 1.01E+03 | 2.94 | 99.89% |
| | None | 4 | 1.82E+05 | | N/A |
| | 2015 | | 5.63E+02 | 2.51 | 99.69% |
| Silicone Rubber | None | 2 | 2.18E+06 | | N/A |
| | 2015 | | 1.08E+03 | 3.30 | 99.95% |
| | None | 4 | 1.45E+06 | | N/A |
| | 2015 | | 2.38E+03 | 2.78 | 99.84% |
| Stainless Steel | None | 2 | 7.05E+05 | | N/A |
| | 2015 | | 1.17E+02 | 3.78 | 99.98% |
| | 2015 (autoclaved) | | 6.32E+03 | 2.05 | 99.10% |

TABLE 4-continued

Results for 2015 coated carriers challenged with *E. aerogenes* ATCC 13048.
2015-Coated Medical Devices Test-*E. aerogenes* ATCC 13048

| Material | Coating | Contact Time | Geo. mean (CFU/carrier) | Log10 Reduction | Percent Reduction |
|---|---|---|---|---|---|
| | None | 4 | 1.02E+05 | | N/A |
| | 2015 | | 6.37E+01 | 3.21 | 99.94% |
| | 2015 (autoclaved) | | 8.99E+02 | 2.06 | 99.12% |

The tables indicate residual antimicrobial efficacy for both the 2015 and 2030 compositions when coated and dried on Nitinol, stainless steel and silicone rubber. Residual efficacy on these hard surfaces has been demonstrated for *S. epidermidis* ATCC 12228 and *E. aerogenes* ATCC 13048. In particular, these examples demonstrate that 316 grade stainless steel medical implements can be coated with an antimicrobial coating composition comprising an organosilane and an amine, and then autoclaved, to provide a residual antimicrobial coating on the implement. This coating procedure could be adopted by hospitals and clinics for prepping medical implements prior to patient use.

Example 2: Dissolving Antimicrobial Coatings for Nitinol Metal and Silicone Rubber Implant and Inserted Device Components The following experiments demonstrate dissolving coatings for various implanted and inserted device surfaces. As discussed, post-surgery complications can be mitigated if an implant, such as a component to an artificial hip or knee, includes surfaces coated with a dissolving antimicrobial composition such that the tissue surrounding the implant is bathed in antimicrobial actives in the day or few days following the surgery. Once the implant has been accepted by the patient's body, the antimicrobial efficacy is no longer needed and is expected to dissipate into the body. Further, a catheter, such as a Foley catheter, benefits from a dissolving antimicrobial coating in that the dissolving coating can mitigate infections around the catheter insertion area, which is quite common. In the following laboratory experiments, coupons previously coated with an antimicrobial composition were soaked in liquids that emulate physiological fluids. As discussed above, the coatings demonstrated are dissolved in 1-7 days time.

General Procedures

This study examined the antimicrobial activity of carriers previously coated with the 2015 or 2030 composition as per above, after exposure to simulated physiological fluid. Two types of sterile carriers (Nitinol and silicone rubber) were cut to the size of 1×1 inch. Either of the two compositions described above, namely 2015 or 2030 formulations, were applied and cured as indicated below. The carriers were immersed in fetal bovine serum with saline for 1 h, 1 day, 3 days, or 7 days. After exposure, the carriers were dried for 1 day and the remaining antimicrobial activity of the surface tested against *E. coli* ATCC 25922 using ASTM E1153 Sanitizer Test Method.

Fetal Bovine Serum (FBS) in Saline

Sterilized saline (0.9% NaCl in deionized $H_2O$) with heat-inactivated 1% FBS.

Coating Procedures: Nitinol with 2030, Nitinol with 2015, and Silicone Rubber with 2015

1. One piece of the carrier was placed in a sterile petri dish.
2. The 2030 or 2015 formulation (1 ml) was pipetted on the carrier.
3. The carriers were left in the petri dish to dry.
4. The coated carriers were placed on a hot plate for 1 hour at 100° C. prior to physiological fluid exposure.

Coating Procedure: Silicone Rubber with 2030

1. Carriers were placed on a hot plate at 100° C.
2. The 2030 formulation (1 ml) was pipetted on the carriers and heated for 2 hours.
3. The dried carriers were removed from the hot plate and transferred individually to petri dishes, prior to physiological fluid exposure.

Physiological Fluid Exposure

The coated carriers were placed in 50 ml conical tubes.

The FBS/saline solution (25 ml) was poured gently on the side of the tube, covering the carrier.

The tubes were placed in the incubator at 37° C. (physiological temperature).

The solution was changed once for the 3-day group and twice for the 7-day group. The fluid in the 1 hour and 1 day exposure groups were not changed.

At the completion of the incubation, the carriers were placed on Kimwipe® layers facing up to dry for 1 day prior to the sanitizer test, described below.

Sanitizer Test

1. A frozen aliquot of *E. coli* ATCC 25922 was thawed. A loop was streaked on a TSA plate and then incubated for 48 hours at 37° C.
2. One colony from the plate was inoculated in 20 ml of TSB and incubated for 24 hours at 37° C.
3. The culture was diluted 1:10 in deionized $H_2O$ with 5% fetal bovine serum (108 CFU/ml).
4. Carriers were inoculated with 0.010 ml of test culture (about $1 \times 10^6$ CFU/carrier) onto the center and spread over the surface area using a sterile bent pipette tip, with care not to spread on to the edges.
5. One set of uncoated control carriers was harvested immediately (zero hour) by immersing in 25 ml of letheen broth, vortexed for 1 min, serially diluted $10^{-3}$ to $10^{-4}$ in PBS buffer, and pour plated with cooling TSA.
6. The carriers were placed in an incubator at 25° C. and 50% humidity. At completion of contact times (2 h for 2030-coated carriers, and 4 h for 2015-coated carriers), the carriers were neutralized as per Step 5. Uncoated and control carriers were pour plated at $10^{-2}$ to $10^{-3}$, and coated carriers were pour plated at 100 to 10-2.
7. The plates were inverted and incubated at 37° C. for 48 hours, and then scored by directly counting colonies.
8. $Log_{10}$ and percent reductions were calculated relative to the timed controls.

Results

In the following tables, Log and percent reduction are compared to time control group (uncoated carriers). N=2 carriers per uncoated control and coated groups. Detection limit—1 bacterium in 25 mL neutralizer broth=25 CFU/carrier. A double asterisk (**) indicates a group not having any microbial growth at the lowest dilution plated. The result should be taken with caution or voided.

Table 5 shows the results for Nitinol and silicone rubber coupons previously treated with the 2030 composition, dried as indicated above, and then soaked in physiological fluid for the exposure times indicated. As shown in the table, the 2030 coating dissolves off the test carriers over the course of about 7-days. This demonstrates the applicability of the coating for medical device implants where it is desired for the antimicrobial actives to dissolve into the tissue surrounding the surgical implant or surrounding the inserted catheter.

TABLE 5

Results for 2030 coated carriers soaked in physiological fluid and then challenged with *E. coli* ATCC 25922
Physiological Fluid Test against *E. coli* ATCC 25922

| Material | Coating | Contact Time | Phys. fluid Exposure | Geo. mean (CFU/carrier) | $Log_{10}$ Reduction | Percent Reduction |
|---|---|---|---|---|---|---|
| Nitinol | None | 0 | None | 2.17E+06 | N/A | |
| | None | 2 | None | 9.39E+04 | N/A | |
| | 2030 | | None | 1.33E+02 | 2.85 | 99.86% |
| | | | 1 hour | 2.89E+04 | 0.51 | 69.19% |
| | | | 1 day | 2.50E+01** | 3.57** | 99.97%** |
| | | | 3 days | 4.40E+03 | 1.33 | 95.31% |
| | | | 7 days | 6.30E+04 | 0.17 | 32.95% |
| Silicone Rubber | None | 0 | None | 2.37E+06 | N/A | |
| | None | 2 | None | 8.00E+05 | N/A | |
| | 2030 | | None | 2.91E+02 | 3.44 | 99.96% |
| | | | 1 hour | 4.86E+03 | 2.22 | 99.39% |
| | | | 1 day | 1.26E+03 | 2.80 | 99.84% |
| | | | 3 days | 2.70E+04 | 1.47 | 96.63% |
| | | | 7 days | 7.21E+05 | 0.05 | 9.84% |

Table 6 shows the physiological fluid soaking results for Nitinol and silicone rubber coupons previously treated with the 2015 composition. As shown in the table, the 2015 coating also dissolves off the test carriers over the course of about 7-days. This demonstrates the applicability of the coating for medical device implants and catheters where it is desired for the antimicrobial actives to dissolve into the tissue surrounding the surgical implant or surrounding the inserted catheter.

TABLE 6

Results for 2015 coated carriers soaked in physiological
fluid and then challenged with *E. coli* ATCC 25922
Physiological Fluid Test against *E. coli* ATCC 25922

| Material | Coating | Contact Time | Phys. fluid Exposure | Geo. mean (CFU/carrier) | $Log_{10}$ Reduction | Percent Reduction |
|---|---|---|---|---|---|---|
| Nitinol | None | 0 | None | 2.17E+06 | N/A | |
| | None | 4 | None | 5.13E+04 | N/A | |
| | 2015 | | None | 6.30E+02 | 1.91 | 98.77% |
| | | | 1 hour | 9.45E+02 | 1.73 | 98.16% |
| | | | 1 day | 8.39E+02 | 1.79 | 98.36% |
| | | | 3 days | 4.95E+03 | 1.02 | 90.35% |
| | | | 7 days | 1.56E+04 | 0.52 | 69.55% |
| Silicone Rubber | None | 0 | None | 2.37E+06 | N/A | |
| | None | 4 | None | 3.37E+05 | N/A | |
| | 2015 | | None | 2.40E+02 | 3.15 | 99.93% |
| | | | 1 hour | 2.99E+03 | 2.05 | 99.11% |
| | | | 1 day | 2.47E+03 | 2.13 | 99.27% |
| | | | 3 days | 2.17E+03 | 2.19 | 99.36% |
| | | | 7 days | 5.69E+04 | 0.77 | 83.11% |

In conclusion, both the 2015 and 2030 compositions dissolve off from both Nitinol and silicone rubber, although it is expected that changes in curing, addition of one or more titanium(IV) species, such as in the form of a second coating comprising a titanium sol-gel, and/or structural changes to the organosilane, will change the durability of the antimicrobial coatings on these materials. In these different ways, the coating can have a controlled dissolution rate for a particular implant and for various patient treatment situations. The results herein demonstrate the usefulness of dissolving coatings from Nitinol implant parts, such as components of hip and knee replacement.

Also apparent from the results is that both the 2015 and 2030 coatings have greater initial residual antimicrobial efficacy on silicone rubber than on Nitinol, and that both the 2015 and 2030 coatings dissolve in a somewhat more controlled fashion from the silicone rubber surface than from the Nitinol surface. These results exemplify, amongst other things, that the 2015 and 2030 compositions are both useful for coating silicone rubber parts intended to be implanted or temporarily inserted into patients, and where antimicrobial effects are desired for the areas surrounding the implant or the insertion point for up to about 7-days. These results demonstrate the coatings are particularly well suited for catheters comprising silicone rubber.

Antimicrobial coating compositions, methods for applying antimicrobial coating compositions to medical implements and medical devices, and residual antimicrobial coatings having prolonged antimicrobial efficacy are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a composition or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

We claim:

1. A method of coating an implantable medical device, the method comprising:
    immersing the implantable medical device in an aqueous composition comprising a mixture of 3-aminopropyltriethoxysilane, triethanolamine and water;
    drying the implantable medical device under ambient conditions to produce a coating on the implantable medical device; and
    curing the coating on the implantable medical device by heating the implantable medical device at between about 100° C. to about 1000° C. to produce a cured coating on the implantable medical device;
    wherein the aqueous composition is of the formulation: 10% v/v 3-aminopropyltriethoxysilane, 0.28% v/v triethanolamine, remainder water; and
    wherein the cured coating on the implantable medical device exhibits a residual antimicrobial efficacy against at least one of S. epidermidis or E. aerogenes.

2. The method of claim 1, wherein the implantable medical device comprises Nitinol, stainless steel, or silicone rubber surfaces.

3. The method of claim 2, wherein curing comprises autoclaving the coated implantable medical device comprising stainless steel at about 121° C. for 20 minutes, wherein the cured coating exhibits about a 4.33 $\log_{10}$ reduction of S. epidermidis ATCC 12228 1 hour after initial inoculation of the coated implantable medical device with S. epidermidis ATCC 12228.

4. The method of claim 2, wherein curing comprises autoclaving the coated implantable medical device comprising stainless steel at about 121° C. for 20 minutes, wherein the cured coating exhibits about a 2.93 $\log_{10}$ reduction of S. epidermidis ATCC 12228 2 hours after initial inoculation of the coated implantable medical device with S. epidermidis ATCC 12228.

5. The method of claim 2, wherein curing comprises heating the coated implantable medical device comprising silicone rubber at about 100° C. for 1 hour, wherein the cured coating exhibits about a 3.81 $\log_{10}$ reduction of S. epidermidis ATCC 12228 1 hour after initial inoculation of the coated implantable medical device with S. epidermidis ATCC 12228.

6. The method of claim 2, wherein curing comprises heating the coated implantable medical device comprising silicone rubber at about 100° C. for 1 hour, wherein the cured coating exhibits about a 2.74 $\log_{10}$ reduction of S. epidermidis ATCC 12228 2 hours after initial inoculation of the coated implantable medical device with S. epidermidis ATCC 12228.

7. The method of claim 2, wherein curing comprises heating the coated implantable medical device comprising Nitinol at about 100° C. for 1 hour, wherein the cured coating exhibits about a 2.68 $\log_{10}$ reduction of S. epidermidis ATCC 12228 1 hour after initial inoculation of the coated implantable medical device with S. epidermidis ATCC 12228.

8. The method of claim 2, wherein curing comprises heating the coated implantable medical device comprising Nitinol at about 100° C. for 1 hour, wherein the cured coating exhibits about a 2.70 $\log_{10}$ reduction of S. epidermidis ATCC 12228 2 hours after initial inoculation of the coated implantable medical device with S. epidermidis ATCC 12228.

9. The method of claim 2, wherein curing comprises autoclaving the coated implantable medical device comprising stainless steel at about 121° C. for 20 minutes, wherein the cured coating exhibits about a 3.60 $\log_{10}$ reduction of E. aerogenes ATCC 13048 1 hour after initial inoculation of the coated implantable medical device with E. aerogenes ATCC 13048.

10. The method of claim 2, wherein curing comprises autoclaving the coated implantable medical device comprising stainless steel at about 121° C. for 20 minutes, wherein the cured coating exhibits about a 3.86 $\log_{10}$ reduction of E. aerogenes ATCC 13048 2 hours after initial inoculation of the coated implantable medical device with E. aerogenes ATCC 13048.

11. The method of claim 2, wherein curing comprises heating the coated implantable medical device comprising silicone rubber at about 100° C. for 1 hour, wherein the cured coating exhibits about a 3.27 $\log_{10}$ reduction of E. aerogenes ATCC 13048 1 hour after initial inoculation of the coated implantable medical device with E. aerogenes ATCC 13048.

12. The method of claim 2, wherein curing comprises heating the coated implantable medical device comprising silicone rubber at about 100° C. for 1 hour, wherein the cured coating exhibits about a 2.08 $\log_{10}$ reduction of E. aerogenes ATCC 13048 2 hours after initial inoculation of the coated implantable medical device with E. aerogenes ATCC 13048.

13. The method of claim 2, wherein curing comprises heating the coated implantable medical device comprising Nitinol at about 100° C. for 1 hour, wherein the cured coating exhibits about a 5.13 $\log_{10}$ reduction of E. aerogenes ATCC 13048 1 hour after initial inoculation of the coated implantable medical device with E. aerogenes ATCC 13048.

14. The method of claim 2, wherein curing comprises heating the coated implantable medical device comprising Nitinol at about 100° C. for 1 hour, wherein the cured coating exhibits about a 4.55 $\log_{10}$ reduction of E. aerogenes ATCC 13048 2 hours after initial inoculation of the coated implantable medical device with E. aerogenes ATCC 13048.

15. The method of claim 1, wherein the implantable medical device comprises a coronary stent or an indwelling urinary catheter.

16. The method of claim 1, wherein the implantable medical device comprises a Nitinol stent, an artificial joint, a component of an artificial joint, a pin, a bone screw, a prosthetic limb, a prosthetic breast, a prosthetic eye, an artificial heart valve, an artificial vessel, a mechanical heart, a pacemaker, a support screen, a staple, an electrical wire, an electrode, or a sensor.

17. The method of claim 1, wherein the coating on the implantable medical device is cured by heating at about 100° C.

18. The method of claim 1, wherein the implantable medical device comprises 316 stainless steel or Nitinol and wherein, after the immersing, the implantable medical device is: (a) allowed to dry under ambient conditions, (b) annealed at from about 100° C. to about 1000° C., and (c) sterilized by autoclaving for 20 minutes at 121° C.

* * * * *